(12) United States Patent
Obata et al.

(10) Patent No.: US 6,855,109 B2
(45) Date of Patent: Feb. 15, 2005

(54) PORTABLE ENDOSCOPE

(75) Inventors: Yoshihiro Obata, Saitama (JP); Hiroshi Sano, Chiba (JP); Junji Usami, Tokyo (JP); Shunichi Ito, Tokyo (JP)

(73) Assignee: PENTAX Corporation, Tokyo (JP)

( * ) Notice: Subject to any disclaimer, the term of this patent is extended or adjusted under 35 U.S.C. 154(b) by 146 days.

(21) Appl. No.: 10/196,153

(22) Filed: Jul. 17, 2002

(65) Prior Publication Data

US 2003/0018238 A1 Jan. 23, 2003

(30) Foreign Application Priority Data

| Jul. 18, 2001 | (JP) | P2001-218043 |
| Jul. 18, 2001 | (JP) | P2001-218109 |
| Sep. 26, 2001 | (JP) | P2001-293478 |
| Oct. 31, 2001 | (JP) | P2001-333796 |

(51) Int. Cl.$^7$ .............................................. A61B 1/12
(52) U.S. Cl. .................... 600/158; 600/156; 600/101
(58) Field of Search ................... 600/156, 157, 600/158, 159, 101

(56) References Cited

U.S. PATENT DOCUMENTS

| 5,588,950 A | 12/1996 | Sano et al. |
| 5,674,183 A | * 10/1997 | Adachi ................... 600/158 |
| 5,743,848 A | 4/1998 | Koeda et al. |
| 5,830,128 A | * 11/1998 | Tanaka ................... 600/158 |
| 5,865,727 A | 2/1999 | Sano et al. |
| 5,924,978 A | 7/1999 | Koeda et al. |
| 6,001,058 A | 12/1999 | Sano et al. |
| 6,004,264 A | 12/1999 | Sano et al. |
| 6,007,485 A | 12/1999 | Koeda et al. |
| 6,033,360 A | 3/2000 | Sano et al. |
| 6,066,090 A | * 5/2000 | Yoon ........................ 600/113 |
| 6,270,454 B1 | 8/2001 | Sano et al. |

* cited by examiner

Primary Examiner—Beverly M. Flanagan
(74) Attorney, Agent, or Firm—Greenblum & Bernstein P.L.C.

(57) ABSTRACT

At the tip of an insert portion of an endoscope, LEDs are provided. An air and liquid supply unit is mounted on a handle portion of the endoscope. The air and liquid supply unit is provided with a tank, a pump, and a battery. Liquid, which is supplied to the tip, is stored in the tank. The battery supplies driving current to the pump and the LEDs. The pump takes in the surrounding air. In accordance with the manipulation of the buttons provided on a grip portion of the endoscope, the pump sends either the liquid or the air to the tip.

27 Claims, 34 Drawing Sheets

FIG. 5
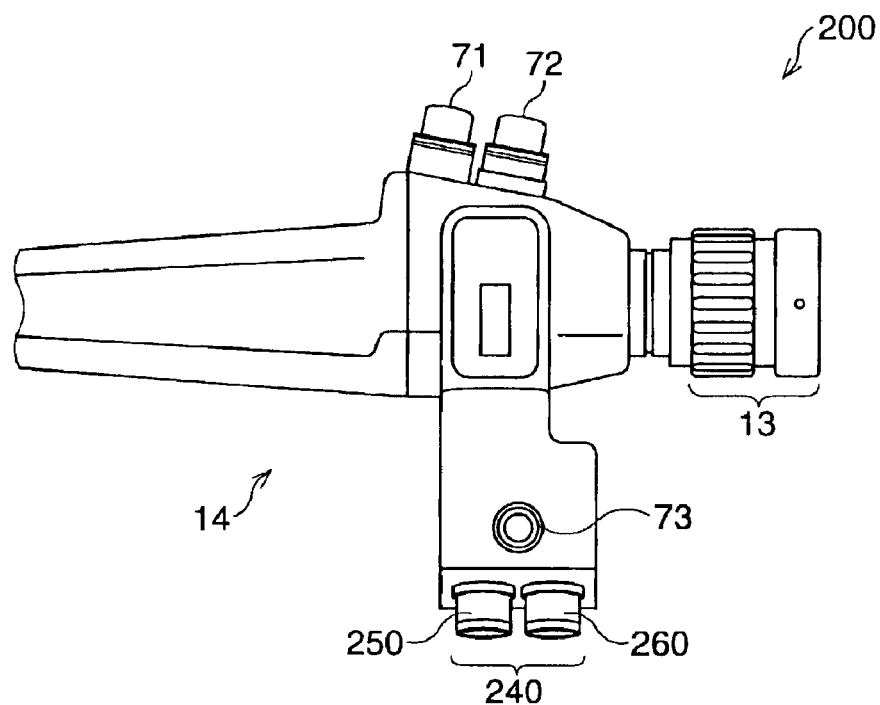
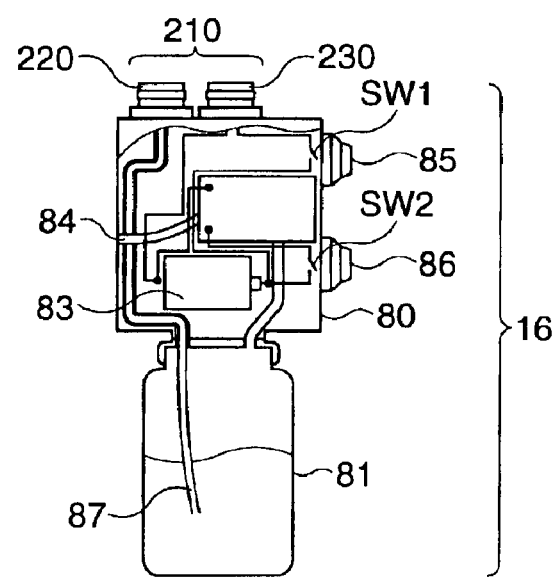

PORTABLE ENDOSCOPE

BACKGROUND OF THE INVENTION

1. Field of the Invention

This invention relates to a portable endoscope which is provided with the functions of supplying gas and liquid.

2. Description of the Related Art

Conventionally, when an endoscope is used, the endoscope is connected to a light source device. When the endoscope is connected to the light source device, a light guide, which is provided so as to penetrate in the endoscope, is optically connected with the light source. For example, a halogen lamp is utilized for the light source. A luminance flux, which is emitted from the light source, is led to a distal end of the endoscope through the light guide. The luminance flux is emitted from the tip of the distal end to illuminate an object in front of the tip. The luminance flux reflected by the object, becomes incident on an image guide through an objective lens which is provided at the tip. The reflected luminance flux is led to an eyepiece portion of an operating portion of the endoscope. Accordingly, the object can be sighted through the eyepieces of the eyepiece portion.

Further, the endoscope is provided with the functions of supplying gas and liquid. By manipulating a button for each function, which is provided on the operating portion, gas and liquid spout from the tip of the scope. Accordingly, an object, attached to the surface of an observing window for protecting the above-mentioned objective lens, can be removed; the gas is sent into a body of a patient; and the surface of the observing window is cleaned.

The liquid, which is sent to the tip of the scope, is stored in a tank, which is not included in the endoscope. The tank is connected to a supplying tube, which enters the channel of an insert portion of the endoscope, through an external connecting tube. Supplying the gas and liquid is carried out by a pump which is provided in the light source device.

As described above, when the endoscope is used, the external devices (the light source device and the tank) are needed. Therefore, the external devices should always be carried with the endoscope, and before operating the endoscope, an operator should make sure the external devices are connected to the endoscope. Namely, with respect to portability, the conventional endoscope has problems.

Further, the insert portion of the scope is manipulated and inserted into the body of patient, therefore ease of handling is required. However, as described above, the light source device and the tank should be connected with the endoscope through cables, and the light source device should be connected to a power outlet through a power cable in order to supply a driving current to the light source and the pump which are provided in the light source device.

Namely, a plurality of cables are required, and these cables prevent the operator from easily handling the endoscope.

Further, the light source device is an external device which is put into one position, and can not be freely moved in accordance with the manipulation of the scope. Additionally, the power cable is connected with the power outlet which is placed at a predetermined position of a consultation room and so on. Accordingly, the endoscope is restricted to the area in which the power outlet is located. Namely, with respect to handling, the conventional endoscope has many problems.

SUMMARY OF THE INVENTION

Therefore, an object of the present invention is to provide an endoscope which has excellent portability and convenience of handling.

In accordance with an aspect of the present invention, there is provided a portable endoscope comprising: a semiconductor light-emitting element that is provided at a tip of an insert portion of a scope in order to illuminate the area to be observed; and a supply unit. The supply unit includes: a pump which supplies gas and liquid to the tip; a power supplying apparatus which supplies power to the semiconductor light-emitting element and the pump; and a tank in which the liquid is stored. The supply unit is provided on a handle portion of said scope.

According to the present invention, the semiconductor light-emitting element is provided at the tip of the insert portion of the scope, and the supply unit is provided at the handle portion of the scope. Namely, it is unnecessary to connect any external devices to the scope through cables. Accordingly, the portability of the fiber scope is improved. Further, the handling of the scope is not disturbed by cables. Therefore, the convenience of using of the scope is improved.

Optionally, the supply unit is attachably and detachably mounted on said handle portion. Preferably, the tank and the pump are symmetrically arranged along a longitudinal axis of the handle portion.

When the supply unit is attachably and detachably mounted on the handling portion, the effects described below can be obtained. Namely, if the supply unit malfunctions, due to, for example, use for a long time, the scope can continue to be used by simply attaching a new supply unit. Accordingly, it is economical. Further, if the supply unit malfunctions while the scope is being used in a patient, the situation can be quickly resolved by attaching a new supply unit.

Further, when the tank and the pump, which are comparatively heavy devices, are symmetrically arranged along the longitudinal axis of the handle portion of the scope, the balance of the scope can be maintained. Accordingly, operation of the endoscope can be carried out with ease while an operator is holding the handle portion, and the convenience of handling the scope is improved because no external devices are attached.

Preferably, the handle portion includes a grip portion that is gripped by the operator and a linking portion that links the grip portion and the insert portion, and the tank and the pump are fixed in the linking portion, and the power supplying apparatus is mounted in the grip portion so as to extend in a direction perpendicular to the longitudinal axis of the handle portion.

When the tank and the pump are fixed at the linkage portion which links the insert portion and the grip portion, these devices are positioned below the hand of the operator. Accordingly, stability of the scope during operation is improved more.

Preferably, the supply unit includes a supply unit connector that has enclosed type valve mechanisms, and the handle portion includes a handle portion connector that has valve opening mechanisms. Each of the enclosed type valve mechanisms includes: a valve body; a holding member which holds the valve body, the holding member having an opening; an urging member which is provided in the holding member and urges the valve body such that the opening is closed. Each of the valve opening mechanisms includes a projecting member which presses the valve body in a direction opposite to a direction of the urging force of the urging member, when the supply unit is attached to the handle portion.

When the supply unit is detached from the handle portion of the scope, the opening of the holding member of each of the enclosed type valve mechanisms is closed by the valve body. Accordingly, if the scope is cleaned and disinfected without protecting caps attached to the supply unit connectors, washing liquid and liquid medicine do not get into the pump and hence the pump does not break.

Further, since it is unnecessary to use protecting caps for the supply unit connectors, the operations of cleaning and disinfecting are facilitated.

BRIEF DESCRIPTION OF THE DRAWINGS

The objects of the present invention will be better understood from the following description, with reference to the accompanying drawings, in which:

FIG. 5 is an external view of a portable endoscope to which a second embodiment, according to the present invention, is applied;

DESCRIPTION OF THE PREFERRED EMBODIMENTS

Figure 1:
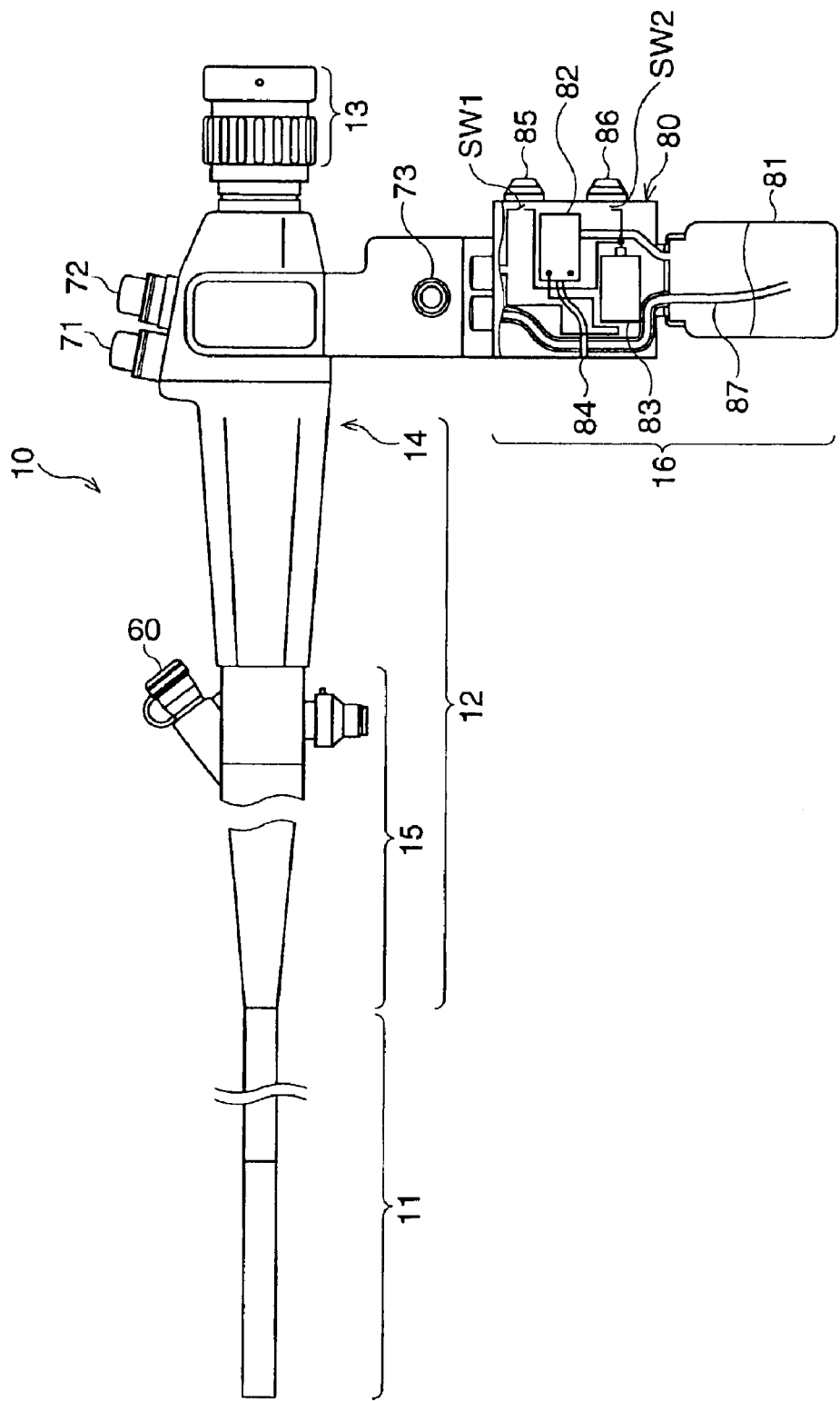
FIG. 1 is an external view of a portable endoscope to which a first embodiment, according to the present invention, is applied.

The present invention will now be described with reference to embodiments shown in the drawings.

FIG. 1 is an external view of a portable endoscope to which a first embodiment according to the present invention is applied, with some portions broken away for clarity.

A fiber scope 10 includes an insert portion 11, a handle portion 12, and an eyepiece portion 13. The insert portion 11 is a flexible conduit which is inserted into a body of a patient. Various operating buttons are provided at the handle portion 12. The eyepiece portion 13 is unitarily formed with the handle portion 12. The handle portion 12 includes a grip portion 14 and a linkage portion 15 which links the insert portion 11 and the grip portion 14.

Figure 2:
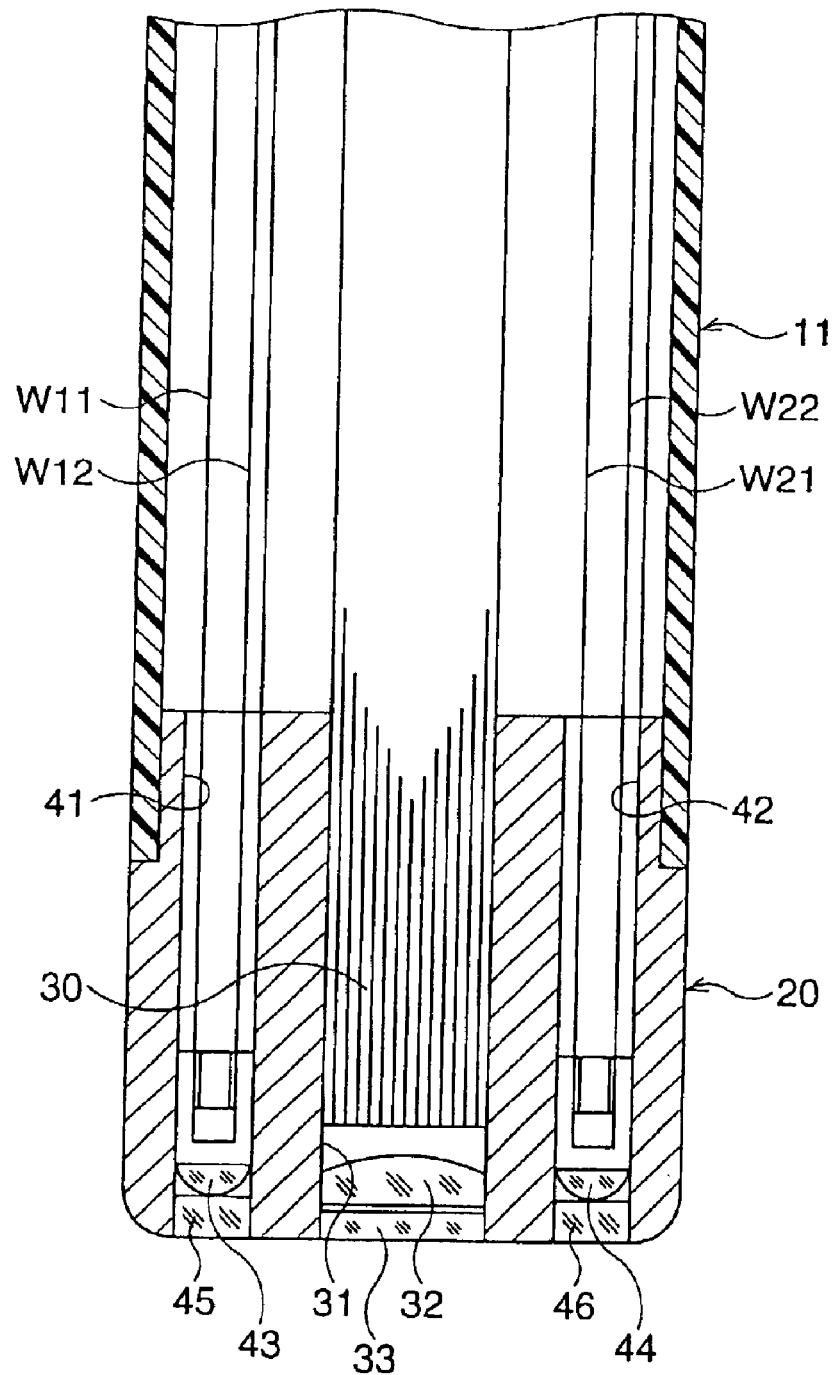
FIG. 2 is an enlarged cross-sectional view of a tip of an insert portion of the endoscope of the first embodiment.

FIG. 2 is a cross sectional view in which a tip of the insert portion 11 is enlarged. A tip member 20, which is made of rigid material, for example corrosion-proof metal, is fixed at an opening of the tip of the insert portion 11. A penetrating hole 31 is formed in the tip member 20. A tip of an image guide 30 which pierces through the insert portion 11 is secured in the penetrating hole 31. An objective lens 32 is provided before the tip of the image guide 30. The image guide 30 is a fiber bundle for transmitting an image which is formed by the objective lens 32. A window 33 is fixed at the opening of the penetrating hole 31, in order to protect the objective lens 32 and to prevent foreign bodies from entering the penetrating hole 31.

Further, in the tip member 20, penetrating holes 41 and 42 are formed along the same section of FIG. 2. LED 43 and LED 44 are respectively provided close to the opening end of the penetrating holes 41 and 42. In the penetrating hole 41, a diffusing optical system 45 is provided in an optical path of the LED 43, and in the penetrating hole 42, a diffusing optical system 46 is provided in an optical path of the LED 44. Driving currents are supplied to the LED 43 and LED 44 through wires W11, W12, W21, and W22.

Figure 3:
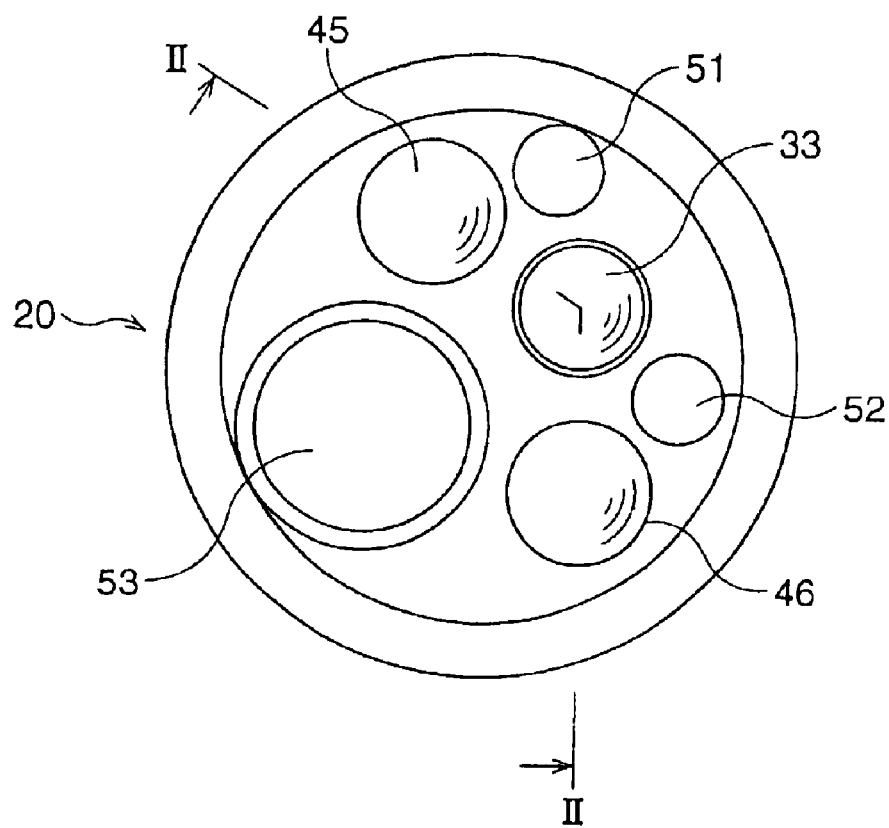
FIG. 3 is a front view of a tip member of the insert portion.

FIG. 3 is a front view of the tip member 20. In FIG. 3, the positional relationship between each element is conceptionally depicted. Note that, the section shown in FIG. 2 corresponds to a sectional view taken in the direction of the arrows substantially along the line II–II of FIG. 3. An air (gas) supply nozzle 51 and a water (liquid) supply nozzle 52 respectively penetrate into an air sending channel and a water sending channel (not shown in FIG. 3) which are formed in the insert portion 11. Air and water for washing the window 33 are respectively spouted from the air supply nozzle 51 and the liquid supply nozzle 52, so that matter, attached to the surface of the window 33, is removed, and the window 33 is washed. A forceps for biopsy can be supplied through the channel 53, so that a sample of tissue of a diseased part can be cut. Note that, procedure for sending air and water to the tip member 20 will be explained after.

As shown in FIG. 1, a forceps port 60, which is connected to the above-mentioned forceps channel 53, is provided at the linkage portion 15. Tools, for example a forceps for biopsy, a brush and so on, are fed to the tip of the insert portion 11, after being inserted in the forceps port 60 and pushed through the forceps channel 53.

Buttons 71 and 72 are provided on the grip portion 14. When an opening (not shown) which is at the top of the button 71 is covered, air is spouted from the air supply nozzle 51 of the tip member 20, so that matter on the window 33 is removed and air is sent into the body. When the button 71 is pushed, liquid is spouted from the liquid supply nozzle 52 of the tip member 20, so that the surface of the window 33 is washed.

A suction tool (not shown in FIG. 1) is connected with the endoscope 10 through a nipple 73. When the button 72 is pushed in a state where the forceps port 60 is plugged, the suction from the opening of the forceps channel 53 is carried out at the tip member 20, so that waterdrops and mucus, attached on the surface of the window 33, are removed and air in the body is sucked out.

A supply unit 16 is provided close to the nipple 73. The supply unit 16 is provided with a main body 80 and a tank 81 in which the above-mentioned liquid is stored. Attached to the handle portion 12, the main body 80 is placed in a position opposite to the buttons 71 and 72, extending in a direction which is perpendicular to the longitudinal direction of the handle portion 12. The main body 80 is fixed to the grip portion 14. Note that, in FIG. 1, the main body 80 is depicted in such a manner that portions are broken away and the inner circuit structure is diagrammatically shown.

A pump 82 and a battery 83 are provided in the main body 80. The pump 82 is connected to an inlet 84 (which is provided on a side surface of the main body 80), the opening of the button 71, the nozzle 51, and the tank 81, through tubes and channels (paths). The pump 82 is a diaphragm pump which sends air, taken in at the inlet 84, to the button 71, the nozzle 51 (see FIG. 3), and the tank 81. The battery 83 supplies driving current to the pump 82, and the LEDs 43 and 44 provided at the tip member 20.

An LED button 85 and a pump button 86 are provided on a side surface of the main body 80. The LEDs 43 and 44 are turned on and off in accordance with manipulation of the LED button 85. The pump 82 is started and stopped in accordance with manipulation of the pump button 86.

A switch SW1 is controlled in accordance with the manipulation of the LED button 85. When the LED button 85 is pushed in a state where the switch SW1 is off, the switch SW1 is turned on, and the supply of the driving current to the LEDs 43 and 44 is started. Accordingly, the LEDs 43 and 44 are turned on, light for illumination is emitted from the tip member 20 through the diffusing optical systems 44 and 45. In this state, when the LED button 85 is pushed again, the switch SW1 is turned off, the driving current supply is stopped, and the LEDs 43 and 44 are turned off.

A switch SW2 is controlled in accordance with the manipulation of the pump button 86. When the pump button 86 is pushed in a state where the switch SW2 is off, the switch SW2 is turned on, and the supply of the driving current to the pump 82 is started, and the pump 82 starts working. Accordingly, air is taken in at the inlet 84 and is sent to the button 71, the nozzle 51, and the tank 81. In this state, when the pump button 86 is pushed again, the switch SW2 is turned off, the driving current supply to the pump 82 is stopped.

When the fiber scope 10 is used, the pump 82 is kept working at all times. If the hole of the button 71 is covered while the pump 82 is working, the air, taken in at the inlet 84, is sent to the nozzle 51, so that the air is spouted from the nozzle 51 as described above. Further, when the button 71 is pushed, an air supply path is closed, the air from the inlet 71 is sent from the pump 82 to only the tank 81, so that air pressure in the tank 81 rises. Consequently, the liquid in the tank 81 is sent through a liquid supply tube 87 which is connected to the nozzle 52, and the water is spouted from the nozzle 52.

Figure 4:
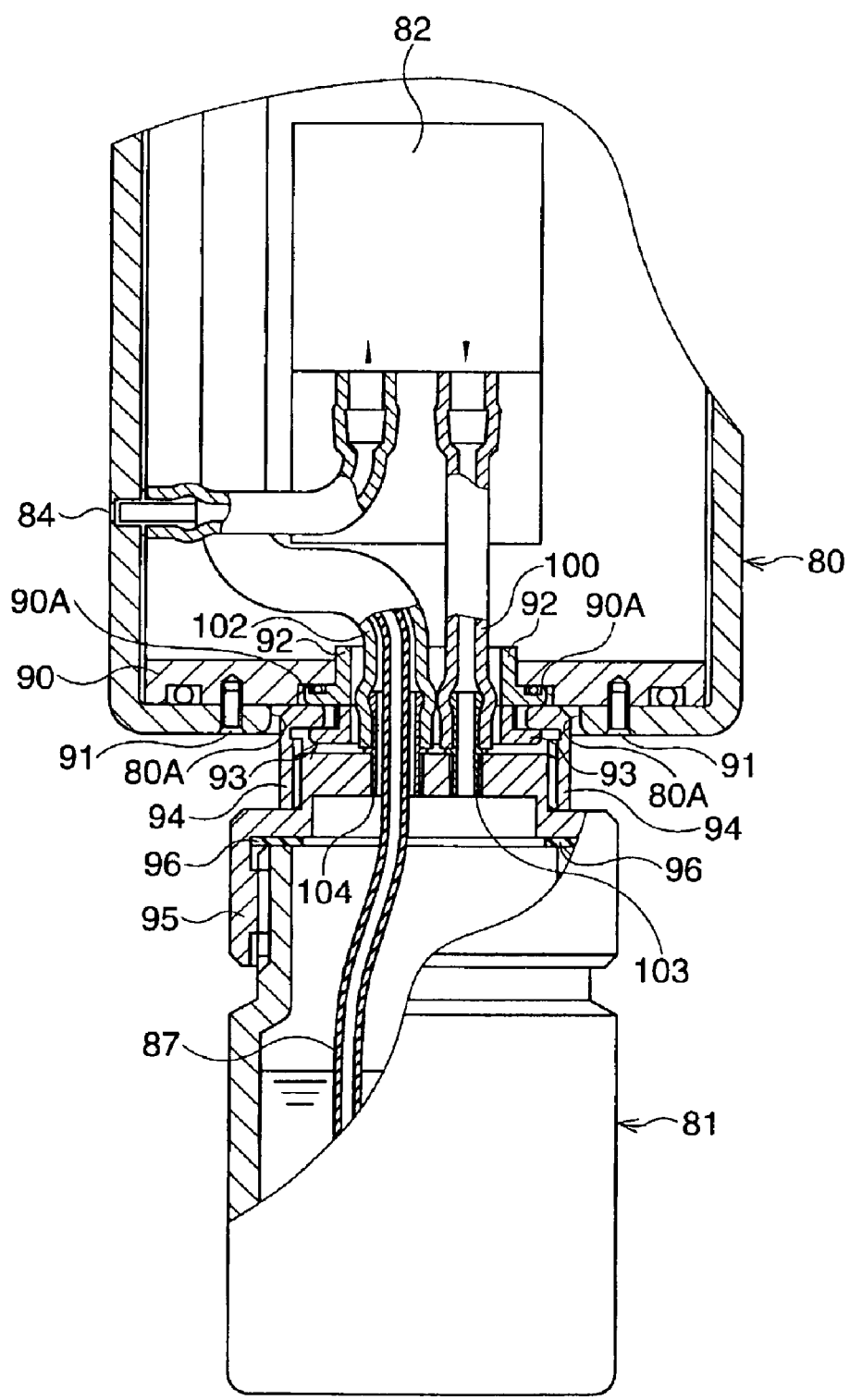
FIG. 4 is an enlarged view which shows a mounting part of a tank and its location.

FIG. 4 is an enlarged view which shows a mounting part of the tank 81 and its vicinity. In the main body 80, an opening 80A is formed at a side surface opposite to the side surface which is fixed on the grip portion 14. A cover member 90 is provided in the main body 80 so as to cover the opening 80A. The cover member 90 is fixed in the body 80 by screws 91. A round opening 90A is formed at the center of the cover member 90. On the inner surface of the opening 90A, a step portion is formed wholly. A tube holder 92 has a shape which is engaged with the step portion, and is mounted in the opening 90A, engaging with the opening 90A.

A stopper 93 is attached to the tube holder 92. In the tube holder 92 and the stopper 93, penetrating holes, the diameter of which are identical, are formed. The stopper 93 is positioned such that the center axes of the penetrating holes are coaxial. A flange is unitarily formed at a free end of the stopper 93. Another stopper 94 is engaged with the flange. A tank cover 95 is engaged with the stopper 94. Further, the tank cover 95 is engaged with the tank 81 through a rubber packing 96.

An air supply tube 100 which is linked to the pump 82, an air supply tube 102 which is linked to the nozzle 51, and the liquid supply tube 87 which is linked to the nozzle 52, pierce through the above-mentioned penetrating holes. The liquid supply tube 87 is provided in the air supply tube 102. Two openings are formed at the bottom of the tank cover 95. Connecting members 103 and 104 are engaged with the openings of the tank cover 95. One end portion of each of the connecting members 103 and 104 is positioned in the penetrating holes of the tube holder 92 and the stopper 93. The air supply tube 100 is engaged with the connecting member 103. The air supply tube 102, which surrounds the liquid supply tube 87, is engaged with the connecting member 104.

FIG. 5 is an external view of a fiber scope 200 to which a second embodiment, according to the present invention, is applied. In FIG. 5, components utilized in the first embodiment, which are identical to those in the second embodiment, share the same reference numerals.

A mounting mechanism 210 of the supply unit 16 is provided on a side surface, of the main body 80, opposite to the side surface on which the tank 81 is mounted. The mounting mechanism 210 is provided with an air and liquid supply cap 220 and an electric connecter cap 230. The caps 220 and 230 have generally cylindrical shape. A mounting mechanism 240 of the handle portion 12 is provided at the grip portion 14, being positioned close to the nipple 73. The mounting mechanism 240 is provided with an air and liquid supply cap 250 which is connectable with the cap 220, and an electric connecter cap 260 which is connectable with the cap 230.

Figure 6:
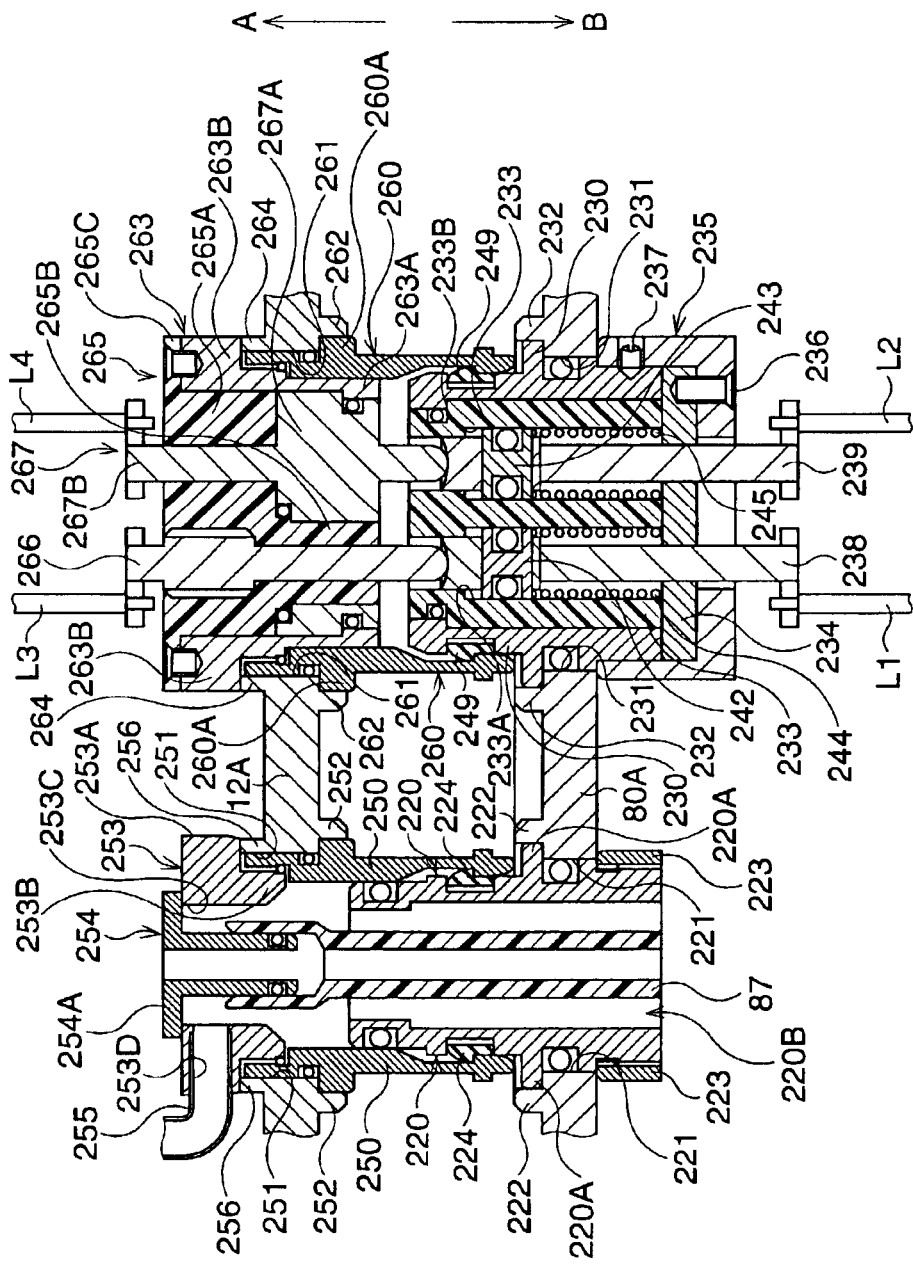
FIG. 6 is a sectional view which shows a connection of mounting mechanisms of a supply unit and a handle portion.

FIG. 6 is a sectional view which shows a connection of the mounting mechanisms 210 and 240. An opening 221 is formed at the side surface 80A of the main body 80 of the supply unit 16. A ring wall 222 is formed so as to surround the opening 221. The cap 220 is engaged with the opening 221 through an O-ring. A flange 220A is formed on the outer surface of the cap 220, projecting in the radial direction of the cap 220. The outer diameter of the flange 220A approximately equals to the inner diameter of the ring wall 222. The cap 220 is situated such that the flange 220A is positioned in the ring wall 222 and one end surface of the flange 220A is in contact with the side surface 80A. Further, a nut 223 is tightly engaged with the cap 220 inside the main body 80, in order to prevent the cap 220 from coming off the opening 221.

An air supply path 220B for sending air is formed in the cap 220, and the tube 87 penetrates through the air supply path 220B. The air supply path 220B is linked to the pump 82 (see FIG. 4) through the tank 81. One end portion of the tube 87 is immersed in the liquid stored in the tank 81 (see FIG. 4).

An opening 251 is formed at the side surface 12A of the grip portion 14. A ring wall 252 is formed so as to surround the opening 251. The cap 250 is engaged with the opening 251 through an O-ring. A fixing member 253 includes a large-diameter portion 253A and a small-diameter portion 253B. A hole 253C pierces through the portions 253A and 253B. The cap 250 and the small-diameter portions 253B are engaged through an O-ring.

A water sending pipe 254 pierces through the handle portion 12 and is linked to the nozzle 52 (see FIG. 3). One end portion of the pipe 254 is provided in the hole 253C. An opening, of the hole 253C, which is at the side of the large-diameter portion 253A, is covered by a flange 254A which is formed on an outer surface of the pipe 254.

A penetrating hole 253D is formed in the portion 253A, extending in the radial direction. At a portion, of the inner surface of the hole 253C, corresponding to the large-diameter portion 253A, the penetrating hole 253D is opened. One end portion of an air sending pipe 255 which is linked to the nozzle 51 is engaged with the penetrating hole 253D.

On the inner surface of the side surface 12A, a projecting portion 256, which has a predetermined height, is wholly formed at the periphery of the opening 251. An outer surface, of the large-diameter portion 253A, which crosses the outer surface of the small-diameter portion 253B, is in contact with the projecting portion 256. Accordingly, the cap 250 is prevented from coming off the grip portion 14.

As shown in FIG. 6, the cap 220 of the mounting mechanism 210 is engaged with the cap 250 of the mounting mechanism 240. In the state where the caps 220 and 250 are engaged, the tube 87 is linked with the nozzle 52 through the pipe 254 and the liquid supply path of the handle portion 12, and the tube 102 is linked with the nozzle 51 through the air supply path 220B, the hole 253C of the fixing member 253, and the air sending pipe 255.

An opening 231 is formed at the side surface 80A of the main body 80 of the supply unit 16, being close to the opening 221. Similar to the opening 221, a ring wall 232 is formed so as to surround the opening 231. The electric connecter cap 230, which has a generally cylindrical shape, is engaged with the opening 231 through an O-ring. A pin holder 233 is provided in the cap 230. The pin holder 233 is made of insulating material, being cylindrical. Two penetrating holes 233A and 233B are formed in the pin holder 233.

An end surface of the cap 230, which is positioned inside the main body 80, and an end surface of the pin holder 233, which is positioned inside the main body 80, form approximately one plane. A covering member 234 is placed so as to be in contact with these end surfaces. Namely, the openings, of the holes 233A and 233B, which are in the main body 80, are covered by the covering member 234. A fixing member 235, which is cup-shaped, is placed so as to cover a portion of the cap 230, which is in the body 80, and the covering member 234. The fixing member 235 is fixed with the covering member 234 at the bottom by a screw 236 and is fixed with the cap 230 at the side by a screw 237.

Bar-shaped connect pins 238 and 239, which are made of conductive material, are respectively provided in the holes 233A and 233B of the pin holder 233. The connect pins 238 and 239 penetrate through holes formed at the bottom of the covering member 234 and the fixing member 235, and the connect pin 238 and 239 are respectively connected with the battery 83 (see FIG. 5) in the main body 80 by lead wires L1 and L2. The diameter of the tip of the connect pin 238 is larger than that of the base body of the connect pin 238. The outer diameter of the tip approximately equals the inner diameter of a small-diameter portion of the hole 233A. Similarly, the diameter of the tip of the connect pin 239 is larger than that of the base body of the connect pin 239. The outer diameter of the tip approximately equals the inner diameter of a small-diameter portion of the hole 233B.

Rings 242 and 243 are respectively fixed at the tip of the connect pins 238 and 239. The outer diameter of the ring 242 approximately equals the inner diameter of a large-diameter portion of the hole 233A, and the outer diameter of the ring 243 approximately equals the inner diameter of a large-diameter portion of the hole 233B. The tip of the connect pin 238 can be slidably moved in the small-diameter portion of the hole 233A along an axis of the hole 233A, and the tip of the connect pin 239 can be slidably moved in the small-diameter portion of the hole 233B along an axis of the hole 233B. Further, the ring 242 can be slidably moved in the large-diameter portion of the hole 233A along the axis of the hole 233A, and the ring 243 can be slidably moved in the large-diameter portion of the hole 233B along the axis of the hole 233B.

In the large-diameter portion of the hole 233A, a coil spring 244 is provided between the covering member 234 and the ring 242 so as to surround the body of the connect pin 238. One end of the coil spring 244 is in contact with the covering member 234 and the other end is in contact with an end surface of the ring 242, so that the coil spring 242 urges the ring 242 in the direction A in FIG. 6, at all times. Accordingly, the connect pin 238 is always urged in the direction A.

Similarly, in the large-diameter portion of the hole 233B, a coil spring 245 is provided between the covering member 234 and the ring 243 so as to surround the base of the connect pin 239. One end of the coil spring 245 is in contact with the covering member 234 and the other end is in contact with an end surface of the ring 243, so that the coil spring 245 urges the ring 243 in the direction A, at all times. Accordingly, the connect pin 239 is always urged in the direction A.

As described above, the outer diameter of the rings 242 and 243 respectively equal the inner diameter of the large-diameter portion of the holes 233A and 233B, being larger than the inner diameter of the small-diameter portion of the holes 233A and 233B. Accordingly, though the rings 242 and 243 are urged in the direction A at all times by the coil springs 244 and 245, the rings 242 and 243 never separate from the opening of the small-diameter portion of the holes 233A and 233B. In other words, the connect pins 238 and 239 are prevented from being excessively urged outward.

An opening 261 is formed at the side surface 12A of the grip portion 14, being close to the opening 251. A ring wall 262 is formed so as to surround the opening 261. The cap 260, which is generally cylindrical, is engaged with the opening 261 through an O-ring. A flange 260A is formed on the outer surface of the cap 260. The outer diameter of the flange 260A approximately equals the inner diameter of the ring wall 262. The cap 260 is mounted on the opening 261, in such a manner that the flange 260A is engaged with the wall ring 262 and the end surface of the flange 260A is in contact with the side surface 12A of the grip portion 14.

A fixing member 263, which is cylindrical, is provided in the cap 260. The fixing member 263 includes a small-diameter portion 263A and a large-diameter portion 263B. The portion 263A is engaged with the cap 260 through an O-ring, and an end surface, of the portion 263B, which crosses the portion 263A, is in contact with a projecting portion 264 which is formed at the periphery of the opening 261.

Therefore, if the cap 260 is pushed or pulled by an external force, neither the cap 260 nor the fixing member 263 move, because they are fixed at the opening 261 of the side surface 12A.

A pin holder 265 which is made of insulation material is provided in the fixing member 263. The pin holder 265 includes a base portion 265A and a projecting portion 265B. The outer diameter of the base portion 265A approximately equals the inner diameter of the fixing member 263. The projecting portion 265B is unitarily formed with the base portion 265A. At the end surface of the base portion 265A, a flange 265C is formed, and the flange 265C is fixed with the fixing member 263 by screws.

A connect pin 266, which is bar-shaped, is provided in a hole which pierces through the base portion 265A and the projecting portion 265B. One end of the connect pin 266 projects from the opening of the projecting portion 265B by a predetermined length, and the other end is connected with a lead wire L3 which is connected with the lead wire W11 of the LED 43 and the lead wire W21 of the LED 44.

A connect pin 267 includes a base portion 267A which is engaged with the fixing member 263. In the base portion 267A, a hole, with which the projecting portion 265B of the pin holder 265 is engaged, is formed, and a connecting portion 267B, which pierces through the base portion 265A of the pin holder 265, is formed. Namely, the pin holder 265 and the connect pin 267 are engaged with each other. The connecting portion 267B is connected with the lead wire L4 which is connected with the lead wire W12 of the LED 43 and the lead wire W22 of the LED 44. Further, a projecting piece is formed on the connecting pin 267 at an opposite side to the connecting portion 267B. The length of the projecting piece equals the length of the end of the connect pin 266 which projects from the opening of the projecting portion 265B.

In the state where the supply unit 16 is mounted on the handle portion 12 as shown in FIG. 6, the end of the connect pin 266 of the cap 260 is inserted into the hole 233A of the cap 230, and the projecting piece of the connect pin 267 of the cap 260 is inserted into the hole 233B of the cap 230.

The length of the above-mentioned projecting portion of the connect pin 266 is determined, such that in a state where the caps 230 and 260 are most deeply engaged, the end of the connect pin 266 is in contact with the end of the connect pin 238, and is able to urge the connect pin 238 in a direction B resisting the urging force of the spring coil 244. Similarly, the length of the projecting piece of the connect pin 267 is determined such that in the sate where the caps 230 and 260 are most deeply engaged, the projecting piece is in contact with the end of the connect pin 239, and is able to urge the connect pin 239 in the direction B resisting the urging force of the spring coil 245. Accordingly, a driving current can be supplied to the LEDs 43 and 44 from the battery 83.

On the outer surface of the middle portion of the cap 220, a groove is formed, and on the outer surface of a portion of the cap 230 close to its end, a groove is formed. A stopper 224 is provided in the groove of the cap 220, and a stopper 249 is provided in the groove of the cap 230. The stoppers 224 and 249 are flexible and ring-shaped. The outer diameter of the stopper 224 is slightly larger than the inner diameter of the end of the cap 250, and the outer diameter of the stopper 249 is slightly larger than the inner diameter of the end of the cap 260.

Accordingly, it is necessary to push the caps 220 and 230 to the corresponding caps 250 and 260 with a predetermined force in order to mount the supply unit 16 to the handle portion 12. Further, a predetermined amount of extracting force is required in order to detach the supply unit 16. Namely, the supply unit 16 is prevented from easily coming off the handle portion 12.

Figure 7:
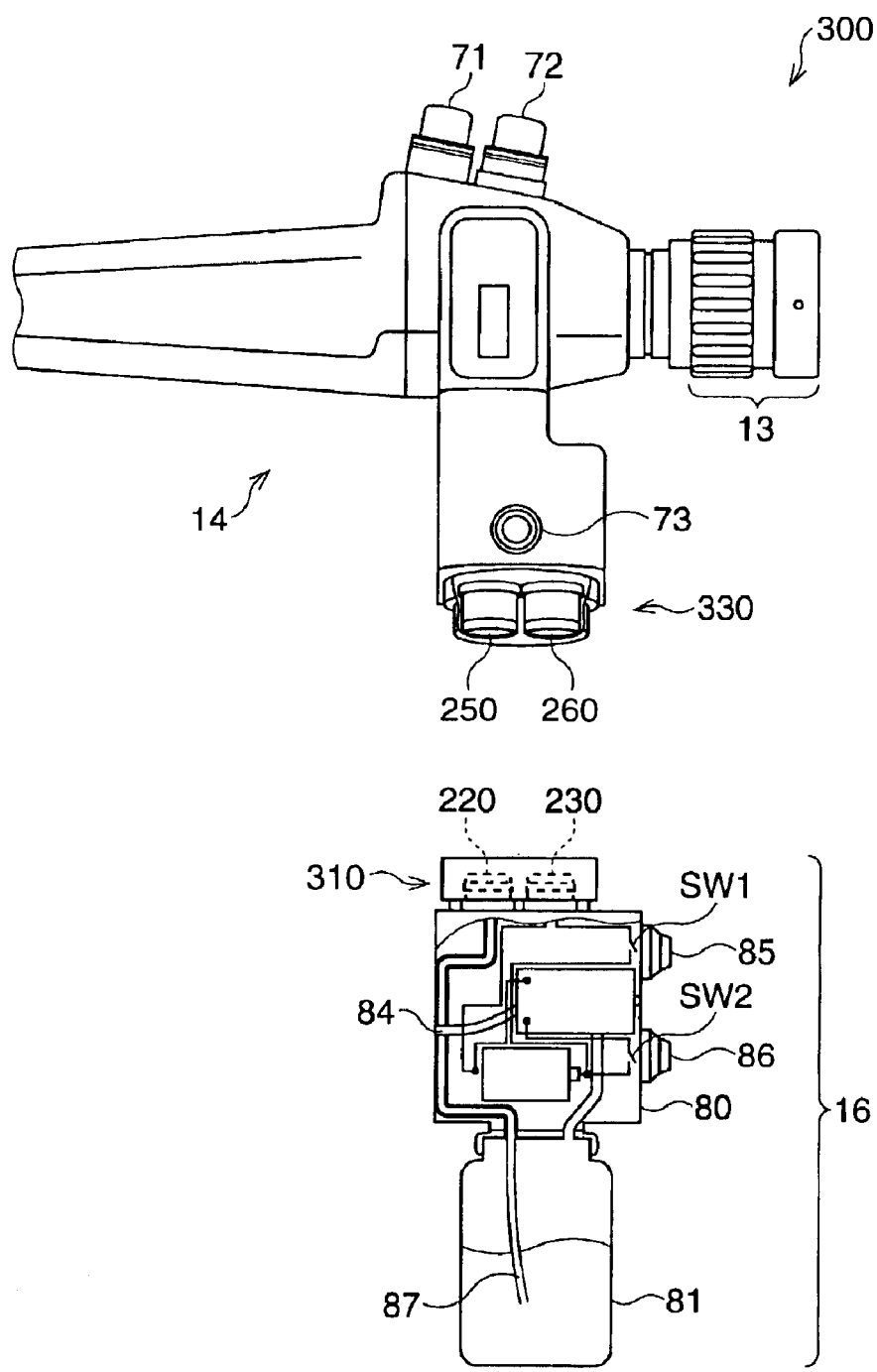
FIG. 7 is an external view of a portable endoscope to which a third embodiment, according to the present invention, is applied.

FIG. 7 is an external view of a fiber scope 300 to which a third embodiment, according to the present invention, is applied, with portions broken away for clarity. In FIG. 7, components utilized in the first and second embodiments, which are identical to those in the third embodiment, share the same reference numerals. A mount supporting mechanism 310 is provided at the supply unit 16 so as to surround the caps 220 and 230. Further, a mount supporting mechanism 330 is provided at the grip portion 14 of the handle portion 12 so as to surround the caps 250 and 260.

Figure 8:
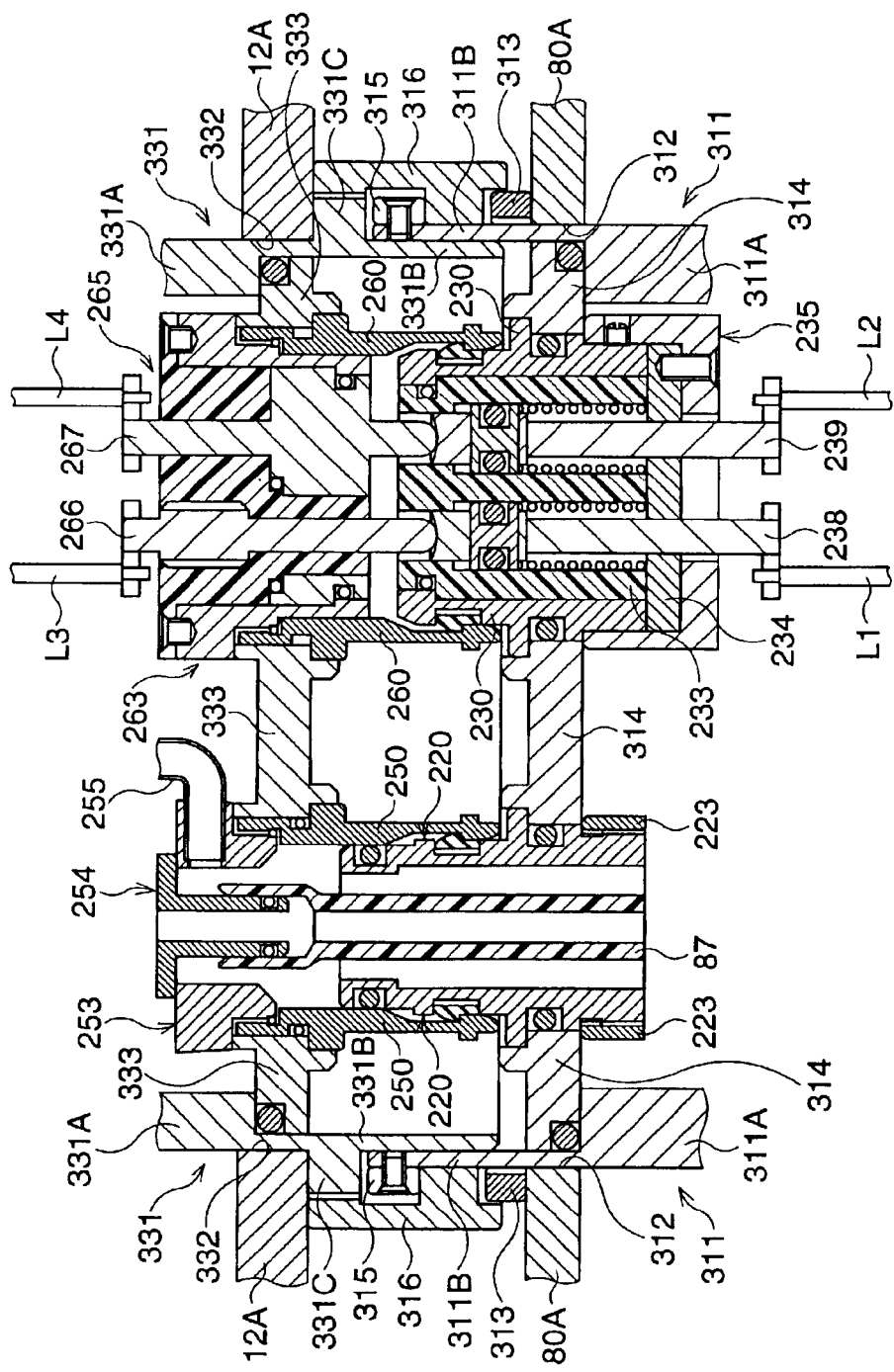
FIG. 8 is a sectional view which shows the connection of mount supporting mechanisms of the supply unit and the handle portion of the third embodiment.

FIG. 8 is a sectional view which shows a connection of the mount supporting mechanisms 310 and 330. In FIG. 8, components utilized in the second embodiment, which are identical to those in the third embodiment, share the same reference numerals.

A support cap 311 includes a cylindrical-shaped base portion 311A and a ring-shaped mounting portion 311B. The mounting portion 311B is unitarily formed at an end surface of the base portion 311A. The mounting portion 311B penetrates through an opening 312 which is formed at the end surface 80A of the main body 80 of the supply unit 16. The outer surface of the mounting portion 311B is fixed to the inner surface of the opening 312. Further, a ring 313 is engaged with the outer surface of the mounting portion 311B, being positioned close to the outer surface of the main body 80.

A holding plate 314 is circular, and the outer diameter of the holding plate 314 approximately equals the inner diameter of the mounting portion 311B. The holding plate 314 is fixed to the end surface, of the base portion 311A, which crosses the mounting portion 311B, through an O-ring. The holding plate 314 holds the caps 220 and 230 similar to those of the second embodiment. Note that, the structure in which the caps 220 and 230 are mounted to the holding plate 314 is similar to the structure in which the caps 220 and 230 are mounted to the side surface 80A in the second embodiment.

Similar to the support cap 311, a support cap 331 includes a cylindrical-shaped base portion 331A and a ring-shaped mounting portion 331B which is unitarily formed at an end surface of the base portion 331A. Further, a flange 331C is unitarily formed on the outer surface of the mounting portion 331B. The support cap 331 is situated such that the mounting portion 331B pierces through an opening 332 which is formed in the side surface 12A, and an end surface of the flange 331C is in contact with the side surface 12A. The outer surface of the mounting portion 331B and the inner surface of the opening 332 are fixed.

Further, the inner diameter of a circular holding plate 333 approximately equals the inner diameter of the mounting portion 331B. The holding plate 333 is fixed at a surface, of the base portion 331A, which crosses the mounting portion 331B. The holding plate 333 holds the caps 250 and 260 similar to those of the second embodiment. Note that, the structure in which the caps 250 and 260 are mounted to the holding plate 333 is similar to the structure in which the caps 250 and 260 are mounted to the side surface 12A in the second embodiment.

As described above, in the third embodiment, the mount supporting cap 311 of the mount supporting mechanism 310 is provided so as to surround the caps 220 and 230, and the mount supporting cap 331 of the mount supporting mechanism 330 is provided so as to surround the caps 250 and 260. The caps 220, 250, 230, and 260 are provided at the corresponding holding plates 314 and 333 such that when the mounting portion 311B of the mount supporting cap 311 and the mounting portion 331B of the mount supporting cap 331 are engaged, the caps 220 and 250 are connected, and the caps 230 and 260 are connected.

Note that, a stopper 316 is fixed on the mounting portion 311B through screws 315. Therefore, when the mount supporting caps 311 and 331 are engaged by a predetermined amount, the end surface of the stopper 316 comes in contact with the side surface 12A, so that the mount supporting caps 311 and 331 are prevented from engaging too much.

According to the third embodiment, the mount supporting cap 311 is provided so as to surround the caps 220 and 230. Accordingly, when the supply unit 16 is sterilized, it is sufficient to mount only one protecting cap, which is capable of simultaneously protecting both the cap 220 and the cap 230 which is linked to the electric power, on the mount supporting cap 311. Namely, some steps for the sterilization can be saved.

Figure 9:
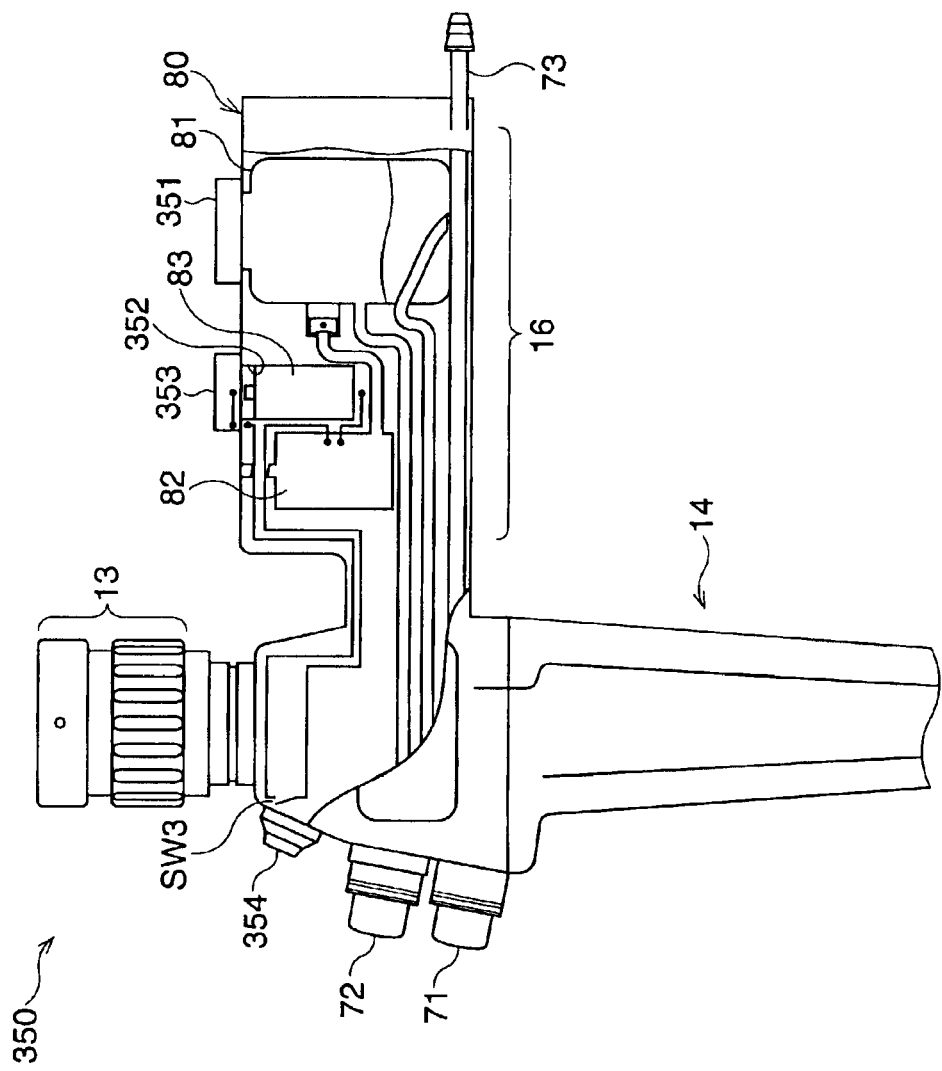
FIG. 9 is an external view partially showing a portable endoscope to which a fourth embodiment, according to the present invention, is applied.

FIG. 9 is an external view partially showing a fiber scope 350 to which a fourth embodiment, according to the present invention, is applied. In FIG. 9, components utilized in the first embodiment, which are identical to those in the fourth embodiment, share the same reference numerals. As is apparent from FIG. 9, the main body 80 is provided at the side of the grip portion 14 of the handle portion 12 opposite to the buttons 71 and 72, extending in a direction which crosses the longitudinal direction of the grip portion 14, and the tank 81 is situated in the main body 80.

A cylindrical mounting portion is provided at the upper side of the tank 81 in FIG. 9. The diameter of the mounting portion is smaller than that of a portion of the tank 81 in which liquid is stored. This mounting portion is mounted to a tank-opening which is formed at the side wall of the main body 80. The tank-opening is covered by attaching a cover 351. When the tank 81 is replenished with the liquid, the cover 351 is detached.

The battery 83 is fixed in a battery holder 352 which is provided in the main body 80. When a cover 353 is attached to an opening of the battery holder 352, the supply of electric current from the battery 83 becomes possible.

A pump button 354 is provided close to the button 72. In accordance with the manipulation of the pump button 354, the state of a switch SW3 is controlled. When the switch SW3 is turned on, driving current is supplied from the battery 83 to the pump 82, and when the switch SW3 is turned off, supply of the driving current is stopped. Note that, the battery 83 is connected with wires (not shown) which are connected with the lead wires W11, W12, W21, and W22 of the LEDs 43 and 44 of the tip of the insert portion 12 of the fiber scope 350, and the circuit between the battery 83 and the LEDs 43 and 44 does not include the switch SW3.

Note that, similar to the fiber scopes 200 and 300 of the second and third embodiments, in the fiber scope 350 of the fourth embodiment, the main body 80 can be made so as to be attachable and detachable.

Figure 10:
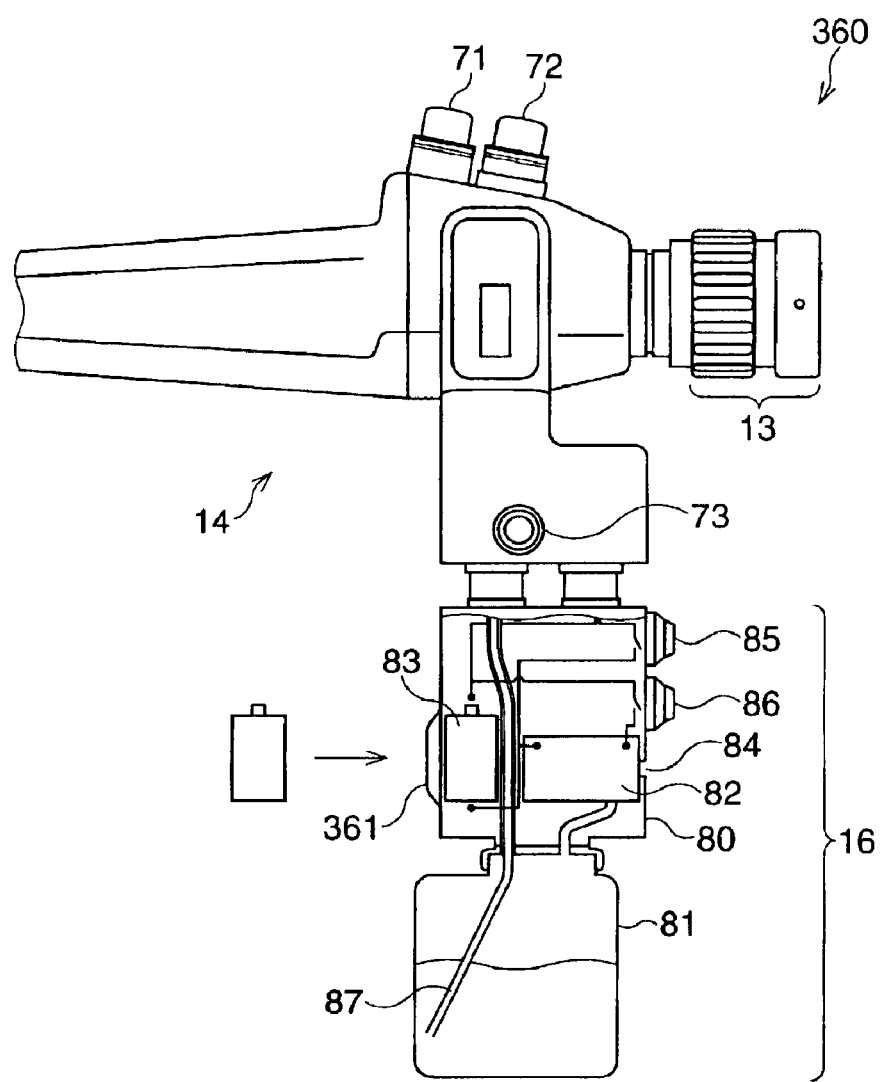
FIG. 10 is an external view of a portable endoscope which is a first modification of the first embodiment.

FIG. 10 is an external view of a fiber scope 360 which is a first modification of the first embodiment. At the main body 80 of the supply unit 16, a battery cover 361 is provided at a side opposite to the side at which the buttons 85 and 86. The buttery cover 361 is a member which protects the battery holder in which the battery 83 is set. The battery cover 361 can be freely opened and closed at the main body 80. The other structures are substantially similar to those of the first embodiment.

According to this modification, replacement of the battery 83 is facilitated. Therefore, if the remaining power of the battery 83 becomes low and it is necessary to get a new battery, the operation of the fiber scope 360 is not stopped for a long time in order to replace the battery 83, so that the load of the patient can be reduced.

Figure 11:
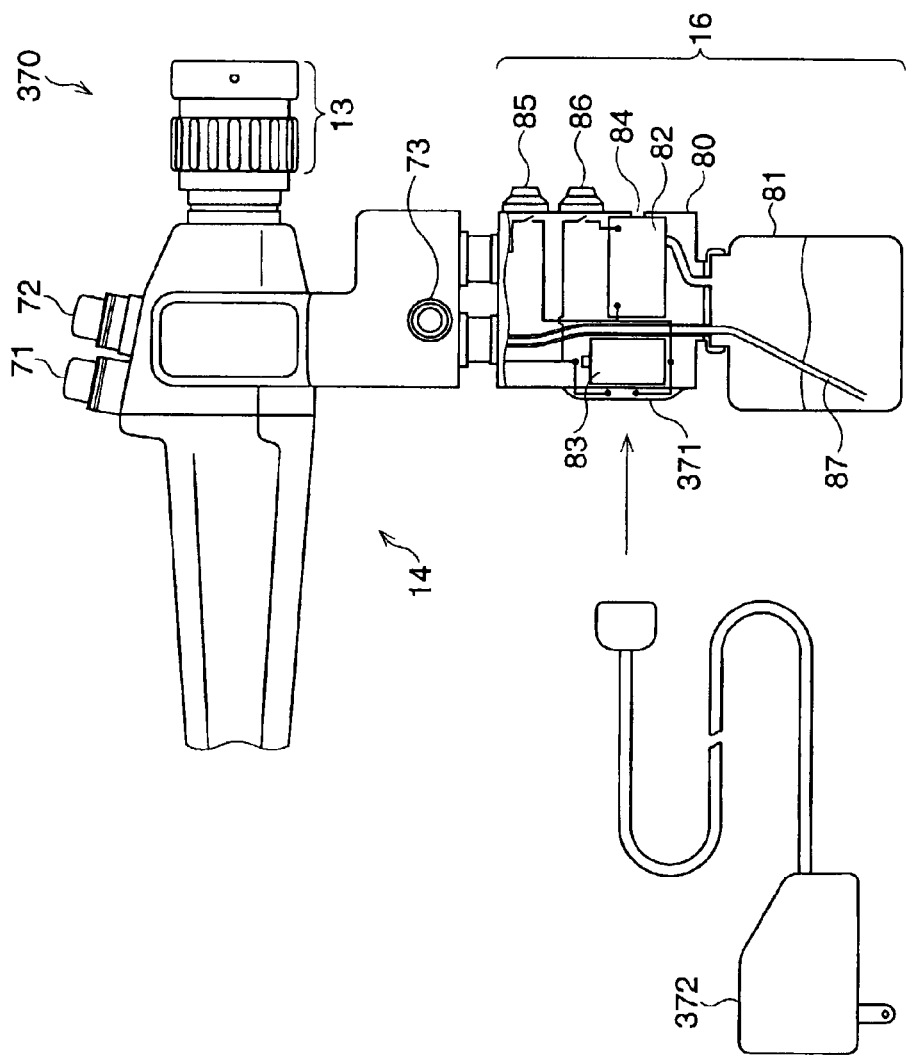
FIG. 11 is an external view of a portable endoscope which is a second modification of the first embodiment.

FIG. 11 is an external view of a fiber scope 370 which is a second modification of the first embodiment. At the main body 80 of the supply unit 16, an adaptor connecting portion 371 is provided at the side opposite to the side at which the buttons 85 and 86 are provided. The well-known AC/DC adaptor 372 can be connected to the adaptor connecting portion 371. An electric circuit in the main body 80 is constructed such that the driving current of the pump 82 and the LEDs 43 and 44 can be supplied from the battery 83 and also can be supplied from a commercially supplied power source through the AC/DC adaptor 372. Accordingly, if the remaining power of the battery 83 becomes low and an extra battery is not prepared, it is possible to continue using the scope by connecting the AC/DC adaptor 372 to the adaptor connecting portion 371.

Figure 12:
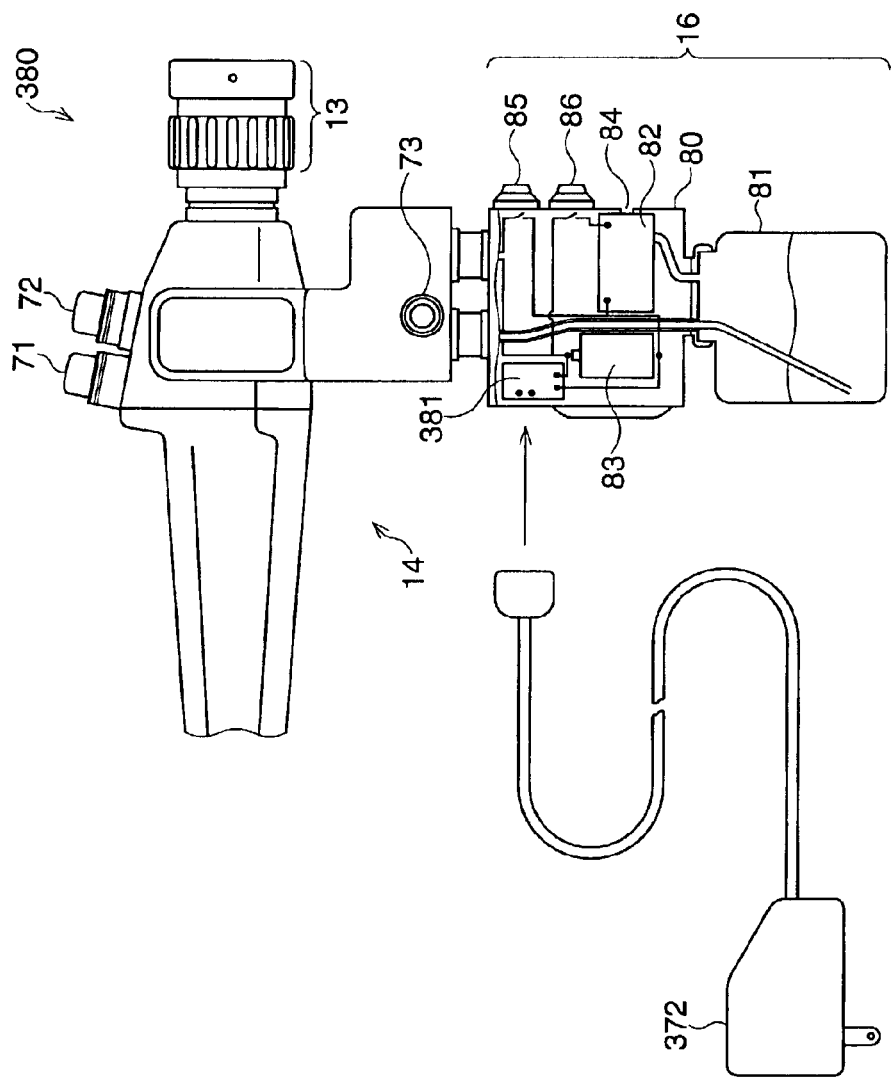
FIG. 12 is an external view of a portable endoscope which is a third modification of the first embodiment.

FIG. 12 is an external view of a fiber scope 380 which is a third modification of the first embodiment. An electric circuit in the main body 80 of the supply unit 16 includes a charging circuit 381. The electric circuit is constructed such that driving current of the pump 82 and the LEDs 43 and 44 can be supplied from the charging circuit 381. Accordingly, after a charging current which is commercially supplied through the AC/DC adaptor 372, the operation of the fiber scope 380 can be continued for a longer time by using both the charging circuit 381 and the battery 83.

Note that, the first through third modifications of the first embodiment can be applied to the fiber scope 200 of the second embodiment, the fiber scope 300 of the third embodiment, and the fiber scope 350 of the fourth embodiment.

According to the first through the fourth embodiments, the lighting devices (the LEDs 43 and 44) are provided at the tip of the insert portion 11 of the fiber scope, and the supply unit 16 and the battery 83 which supplies the driving current of the lighting devices and the supply unit 16 are provided at the handle portion 12 of the fiber scope. Accordingly, the portability of the fiber scope is improved. Further, it is unnecessary to connect the tank 81 and the battery 83 to the fiber scope through cables which disturbs the handling of the fiber scope. Therefore, the convenience of handling of the fiber scope is improved.

Figure 13:
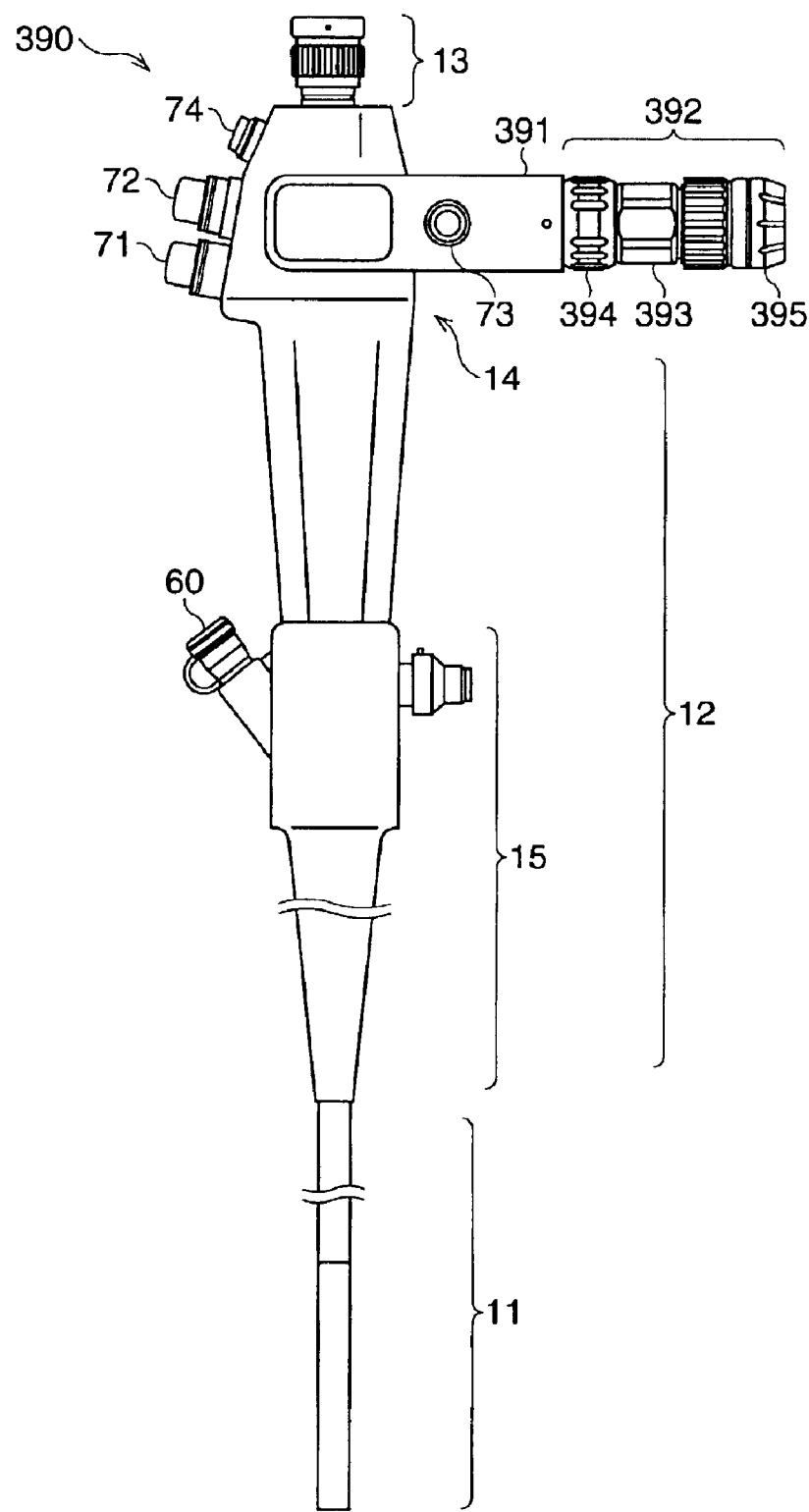
FIG. 13 is an external view of a portable endoscope to which a fifth embodiment, according to the present invention, is applied.

FIG. 13 is an external view of a portable endoscope to which a fifth embodiment, according to the present invention, is applied. In FIG. 13, components utilized in the first embodiment, which are identical to those in the fifth embodiment, share the same reference numerals.

In the fifth embodiment, a button 74 is provided at the grip portion 14, being close to the buttons 71 and 72. Further, at the grip portion 14, an attachment port 391 is provided at the side opposite to the side at which the buttons 71, 72, and 74 are located. A battery unit 392 is attached to the attachment port 391. The battery unit 392 includes a cylindrical housing 393 and a mounting nut 394. By rotating the mounting nut 394, the battery unit 392 can be attached to and detached from the attachment port 391. A battery is provided in the battery unit 392, as described after. In accordance with the rotation of a power button 395, the supply of driving current from the battery is started and stopped.

Note that, the structure of the tip of the insert portion 11 is similar to that of the first embodiment which is depicted in FIGS. 2 and 3.

Figure 14:
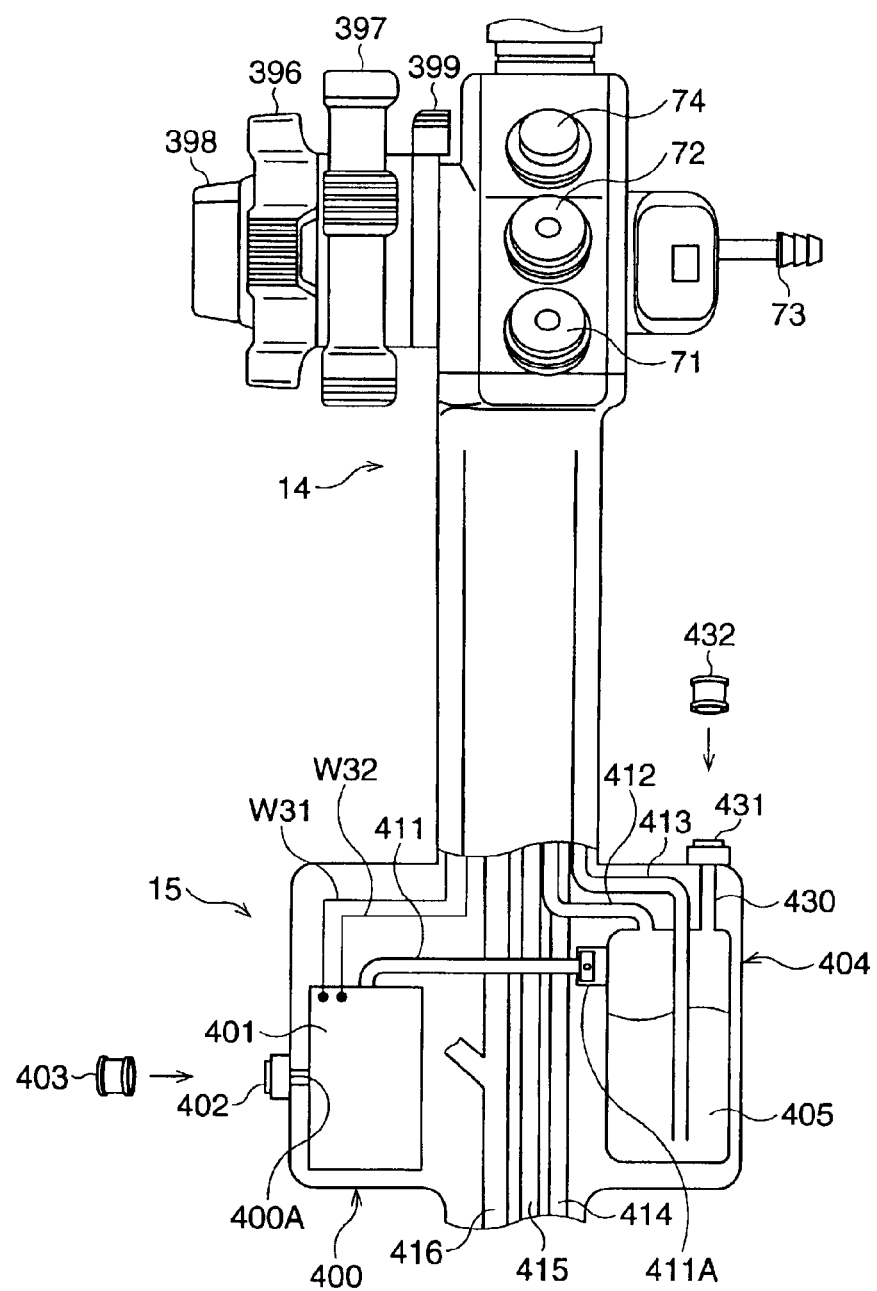
FIG. 14 is an enlarged view which shows a grip portion and a connecting portion of the endoscope of the fifth embodiment.
Figure 15:
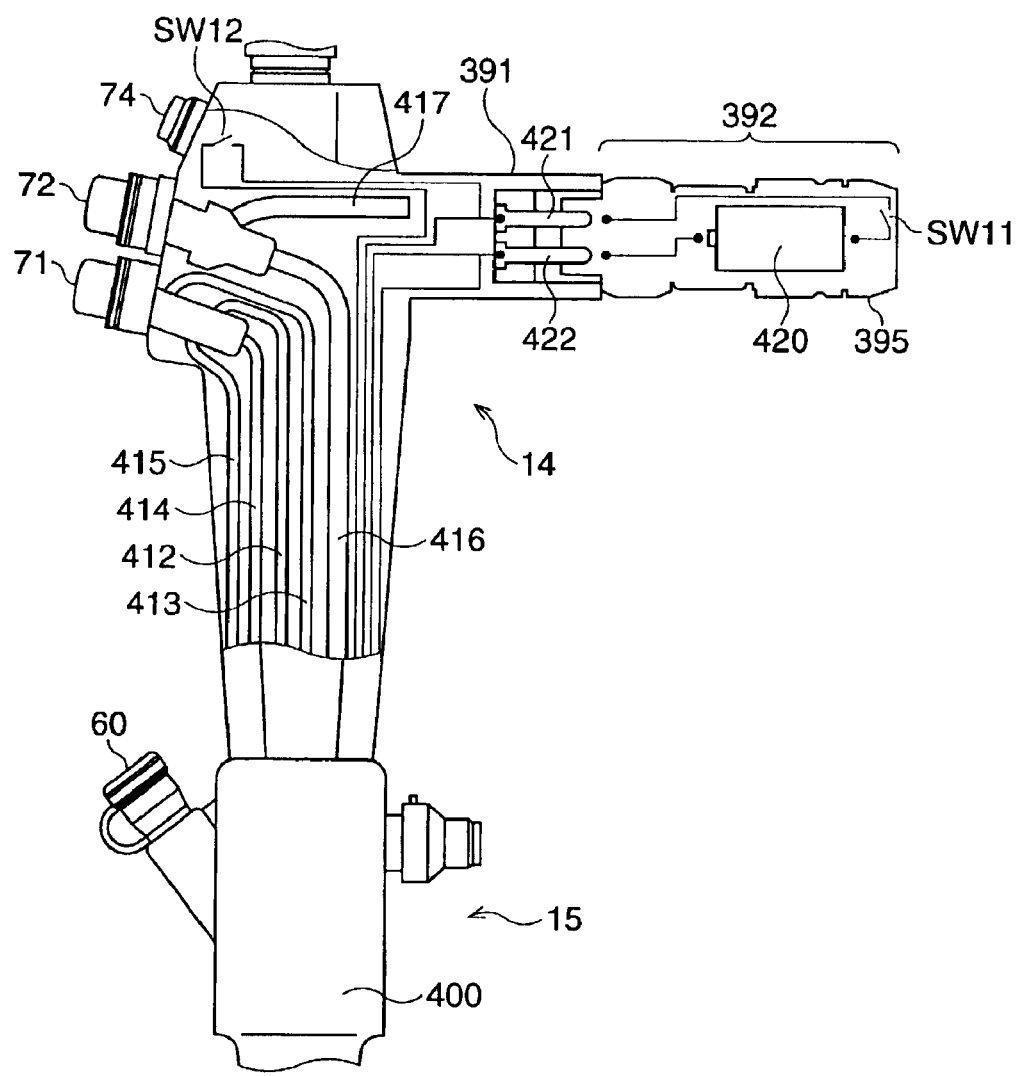
FIG. 15 is an enlarged view which shows the grip portion and a battery unit of the endoscope of the fifth embodiment.

FIG. 14 is an enlarged view which shows the grip portion 14 and the linkage portion 15 at the side at which the above-mentioned buttons of the grip portion 14 are provided. FIG. 15 is an enlarged view which shows the grip portion 14 and the battery unit 392 at the same side as that of FIG. 14. In FIGS. 14 and 15, some portions are broken away for clarity.

When a left-right angle knob 396 and an up-down angle knob 397 are seen at the left side of FIG. 14, these angle knobs have a generally circular shape. These angle knobs are rotatable in the radial direction thereof. When the angle knob 396 is rotated, the tip of the insert portion 11 is curved in a first direction. The angle of the tip in this direction is maintained by manipulating a left-right angle lock lever 398.

When the angle knob 397 is rotated, the tip of the insert portion 11 is curved in a second direction which crosses the first direction. The angle of the tip in the second direction is maintained by manipulating an up-down angle lock lever 399. Note that, the nipple 73 is positioned at the side opposite to the side at which the angle knobs 396 and 397 are provided.

At a portion, of the linkage portion 15, which is adjacent to the grip portion 14, a pump room 400 and a tank room 404 are formed. The pump room 400 is positioned at one side of the longitudinal axis of the grip portion 14 and the tank room 404 is positioned at the other side, opposite to the pump room 400, of the longitudinal axis of the grip portion 14. In other words, the pump room 400 and the tank room 404 are symmetrically arranged with respect to the longitudinal axis of the grip portion 14 so that the grip portion 14 is between them. An air supply pump 401 is set in the pump room 400, and a tank 405 is set in the tank room 404.

Liquid is stored in the tank 405. The air supply pump 401 is connected to an opening 400A which is formed at a side of the pump room 400. An inlet valve 402 is provided at the opening 400A. When the pump 401 is working, an opening cap 403 is mounted to the inlet valve 402 in order to open the inlet valve 402 and take in air from the opening 400A. Note that, a liquid supply pipe 430 is provided at the tank 405, for supplying the liquid. The liquid supply pipe 430 is connected to a liquid supply port 431 which is formed at a side of the tank room 404. When the scope 390 is used, the liquid supply port 431 is closed by a cap 432. The liquid is supplied from the liquid supply port 431 from which the cap 432 is detached.

The air supply pump 401 is connected with the tank 405 through a path 411, so that air, which is taken in from the opening 400A, is sent to the tank 405 through the path 411. The path 411 is provided with a non-return valve 411A which prevents air from flowing from the tank 405 to the pump 401.

An air supply path 412 and a liquid supply path 413 are connected to the tank 401. The path 412 is linked to an air supply path 414, which extends to the tip of the insert portion 11 to supply air to the tip. The path 413 is linked to a liquid supply path 415 which extends to the tip of the insert portion 11 to send the liquid to the tip. One end portion of the path 413 is immersed in the liquid stored in the tank 405. At the tip member 20 (see FIGS. 2 and 3), the path 414 is connected with the nozzle 51 and the path 415 is connected with the nozzle 52.

Similar to the paths 414 and 415, a forceps channel tube 416 extends to the tip of the insert portion 11. This tube 416 is connected with the forceps port 60. Further, the tube 416 is connected with a connecting tube 417 which is connected with the nipple 73, by pushing the button 72. Note that, a connection between the tube 416 and the port 60, and a connection between the tube 417 and nipple 73, are omitted in FIGS. 14 and 15.

When the battery unit 392 is attached to the attachment port 391, a battery 420, which is set in the battery unit 392, is electrically connected with a pair of contact pins 421 and 422, which are provided in the attachment port 391, through a switch SW11. The pair of contact pins 421 and 422 are connected with lead wires W31 and W32 (see FIG. 14) which supply driving current to the pump 401, and with the wires W11, W12, W21, and W22 (see FIG. 2) which are connected with the LEDs 43 and 44 of the tip member 20. The state of the switch SW11 is controlled in accordance with rotation of the power button 395. When the switch SW11 is turned on, driving current is supplied to the LEDs 43 and 44 provided at the tip of the insert portion 11, and it becomes possible to supply driving current to the pump 401.

The state of a switch SW12 is controlled in accordance with pushing action of the button 74. When both the switch SW11 and the switch SW12 are turned on, driving current is supplied to the pump 401.

When the upper hole of the button 71 is covered, the air, which is taken in by the pump 401, is sent to the path 414 through the path 411, the tank 405, and the path 412. Accordingly, as described above, the air is spouted from the air supply nozzle 51 of the tip member 20, so that a mucus on the window 33 is removed and the air is sent into the body.

When the button 71 is pushed, the path 412 and the path 414 are disconnected, and the course, which discharges the air which is sent into the tank 405, is closed. Accordingly, the pressure inside the tank 405 rises, so that the liquid stored in the tank 405 is sent to the path 415 through the path 413. Consequently, as described above, the liquid is spouted from the liquid supply nozzle 52, and in the aforementioned operation, cleaning the surface of the window 33 and so on, is carried out.

Note that, the operations using the button 72, the forceps port 60 and so on are carried out in a similar to those in the first embodiment.

As described above, according to the fifth embodiment, the external devices, for example, the battery 420, the tank 405, the pump 401 and so on, are mounted in the handle portion 12 of the fiber scope 390, and further, the pump 401 and the tank 405 which are comparatively heavy devices are symmetrically arranged with the longitudinal axis of the grip portion 14 between. Therefore, while the operator holds the fiber scope 390, the balance of the fiber scope 390 is easily maintained, and the operation can be stably carried out.

Figure 16:
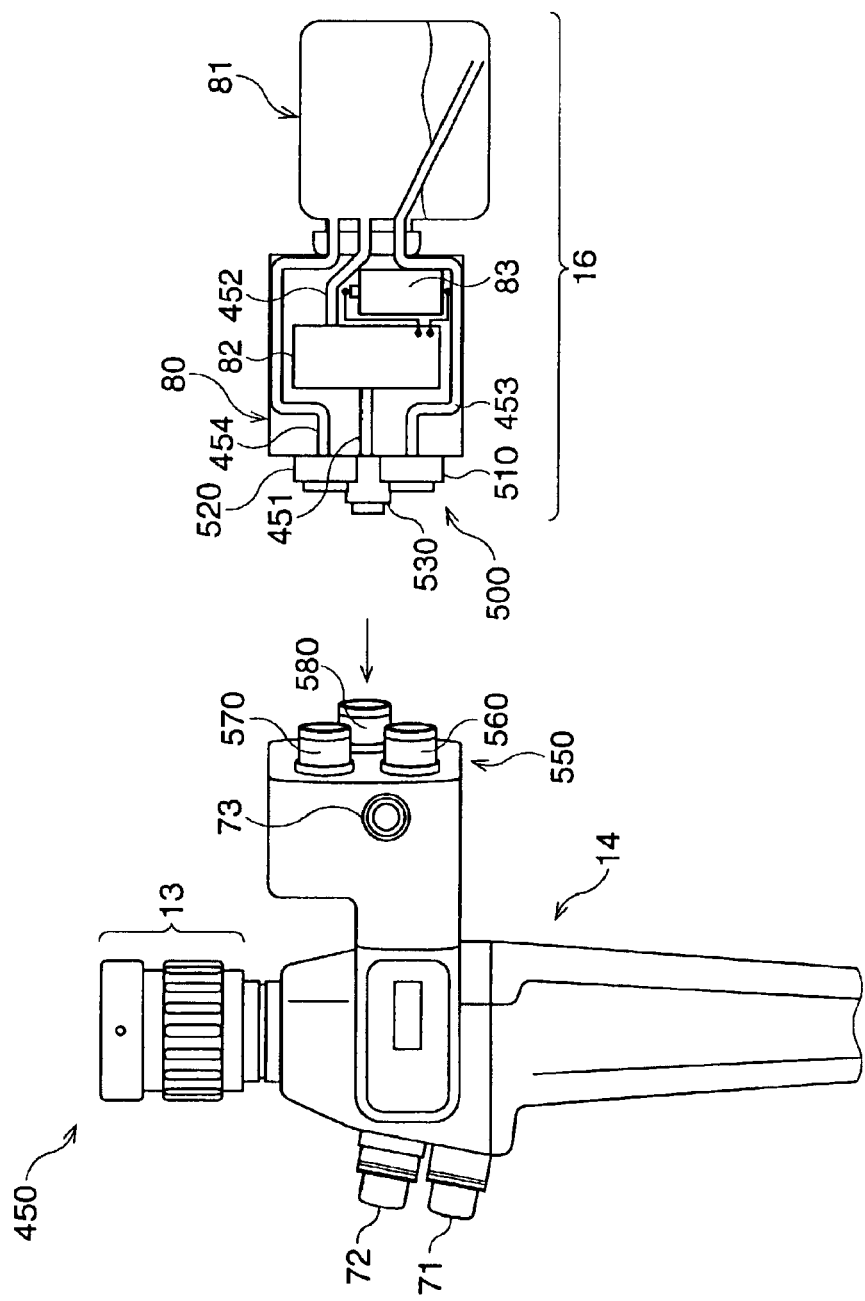
FIG. 16 is an enlarged view of a portable endoscope 450 to which a sixth embodiment, according to the present invention, is applied.

FIG. 16 is an enlarged view of a portable endoscope 450 to which a sixth embodiment, according to the present invention, is applied. Components utilized in the first embodiment, which are identical to those in the sixth embodiment, share the same reference numerals in FIG. 16. Note that, the insert portion 11 and the linkage portion 15 of the handle portion 12 are omitted in FIG. 16, however there structures are identical with those of the first embodiment as shown in FIG. 1. Further, the tip of the insert portion 11 is also identical with that of the first embodiment as shown in FIGS. 2 and 3. Further, in FIG. 16, some portions of the supply unit 16 are broken away for clarity.

An inlet tube 451 is connected to an inlet (not shown) which is formed at a side, of the supply unit 16, which is adjacent to the handle portion 12. Air, which is taken in from the inlet, is sent to the tank 81 through the inlet tube 451. Further, the pump 82 is connected with the tank 81 through an air supply tube 452. Note that, an explanation of the other members, the reference numerals of which are identical with those of the first embodiment, is omitted.

A supply unit connecting mechanism 500 is provided at the side surface of the main body 80. The connecting mechanism 500 includes a liquid supply path connector 510, an air supply path connector 520, and an inlet connector 530. The connector 510 is connected with a liquid supply tube 453 which is provided in the tank 81. The connector 520 is connected with the tank 81 through an air supply tube 454. The connector 530 is connected with the pump 82 through the inlet tube 451.

At the grip portion 14, a handle portion connecting mechanism 550 is provided at a side surface which is close to the nipple 73. The connecting mechanism 550 includes a liquid supply cap portion 560, an air supply cap portion 570, and an inlet cap portion 580. When the supply unit 16 is mounted on the handle portion 12, the connecter 510 and the cap portion 560, the connector 520 and the cap portion 570, and the connector 530 and the cap portion 580, are respectively connected.

Figure 17:
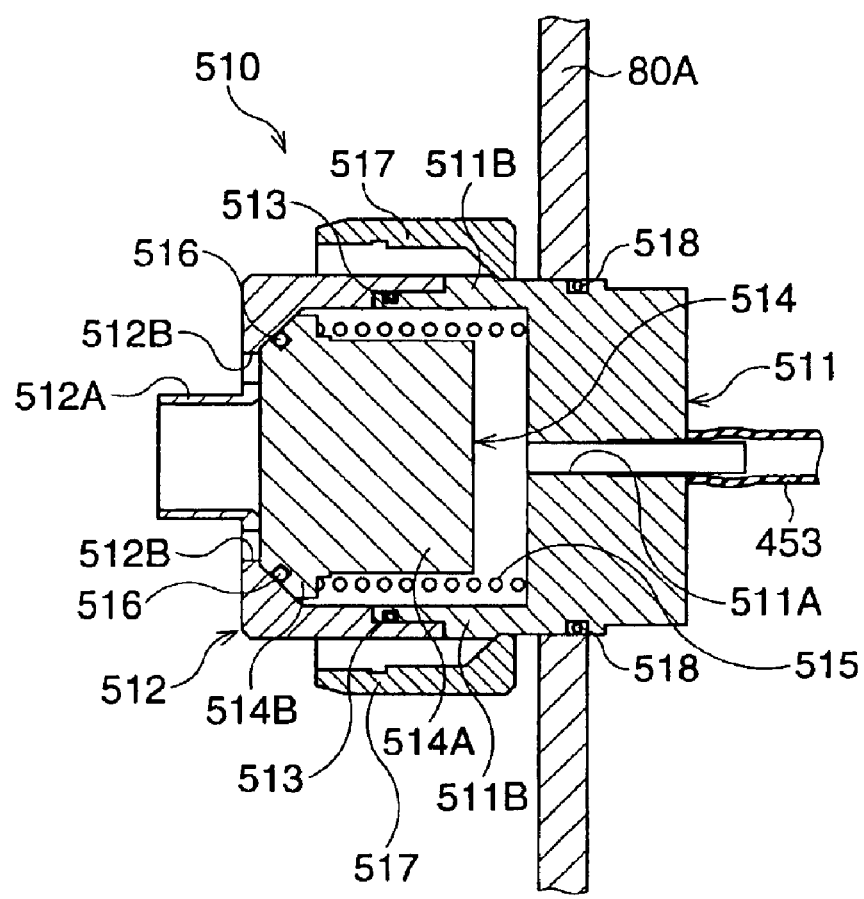
FIG. 17 is a longitudinal sectional view of a liquid supply path connector of the sixth embodiment.

FIG. 17 is a longitudinal sectional view of the liquid supply path connector 510. A cylindrical fixing member 511 is fixedly engaged with a hole which is formed in the side surface 80A of the main body 80. An O-ring 518 is provided between the fixing member 51 and the side surface 80A, so that the engagement of the fixing member 511 and the side surface 80A is watertight. A penetrating hole 511A is formed in the fixing member 511. The liquid supply tube 453 is connected with the hole 511A through a connecting member.

A wall portion 511B, which has a predetermined height, is unitarily formed on a periphery of one end surface of the fixing member 511. The end surface and the wall portion 511B together form a recess portion. A cylindrical covering member 512 is engaged with the wall portion 511B. An O-ring 513 is provided between the wall portion 511B and the covering member 512, so that the engagement of the wall portion 511B and the covering member 512 is watertight.

An opening is formed at the center of the bottom of the covering member 512. An engaged portion 512A, which is ring-shaped, is formed at the periphery of the opening. The engaged portion 512A projects in a direction opposite to the fixing member 511 by a predetermined amount. Further, at the bottom of the covering member 512, two holes 512B are formed around the engaged portion 512A.

A valve body 514 is situated in a space which is formed by the above-mentioned recess portion of the fixing member 511 and a hollow of the covering member 512. The valve body 514 is generally cylindrical. The outer diameter of a base portion 514A of the valve body 514 is slightly smaller than the inner diameters of the fixing member 511 and the covering member 512, so that a gap exists between the fixing member 511, the covering member 512 and the base portion 514A. The shape of a pushed portion 514B of the valve body 514 and the shape of an inner wall of the bottom of the covering member 512 and its vicinity are complementary to each other.

A coil spring 515 is provided around the outer surface of the base portion 514A of the valve body 514. One end of the coil spring 515 is in contact with the bottom of the recess portion of the fixing member 511, and the other end of the coil spring 515 is in contact with the pushed portion 514B of the valve body 514. The coil spring 515 urges the valve body 514 to the left of FIG. 17. Accordingly, without external force, the opening of the covering member 512 is closed by the valve body 514 at all times.

Further, an O-ring 516 is provided at a portion of the pushed portion 514B which is in contact with the covering member 512 while the valve body 514 is urged by the coil spring 515. Accordingly, the connection between the valve body 514 and the covering member 512 is watertight, when the valve body 514 covers the opening of the covering member 512 with the urging force of the coil spring 515.

A mounting ring 517 is fixed on the outer surface of the wall portion 511B of the fixing member 511. The mounting ring 517 is arranged such that a predetermined gap exists between the wall portion 511B, the covering member 512 and the mounting ring 517.

Figure 18:
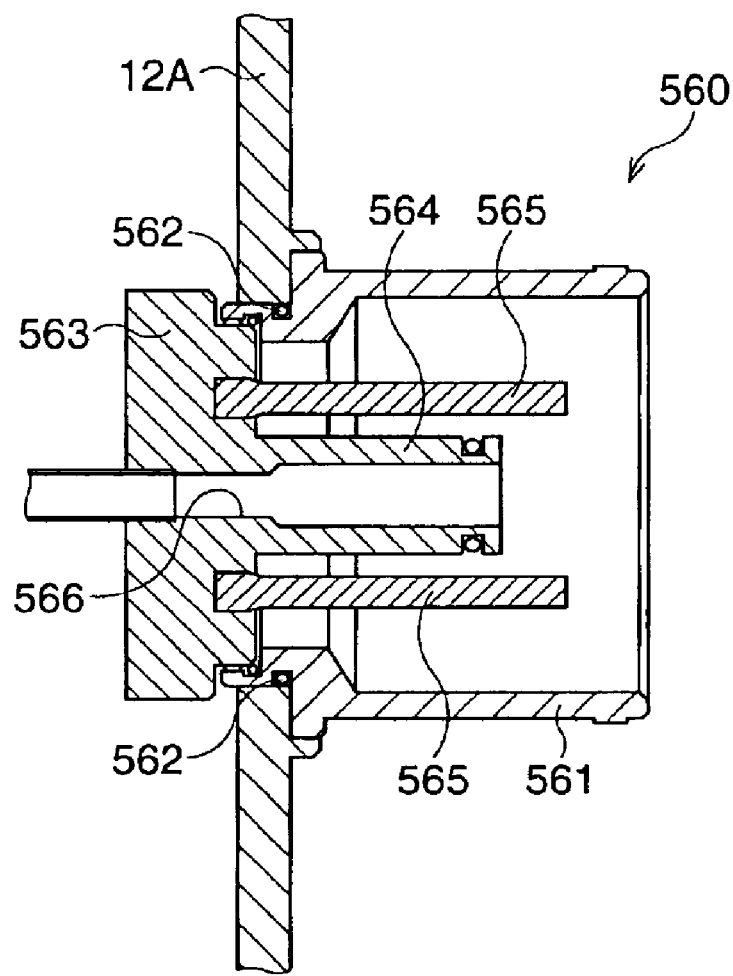
FIG. 18 is a longitudinal sectional view of a liquid supply cap portion of the sixth embodiment.

FIG. 18 is a longitudinal sectional view of the liquid supply cap portion 560. A cylindrical cap 561 is provided at the side surface 12A of the grip portion 14. A portion close to an opening of one end of the cap 561 is fixed to the side surface 12A through an O-ring 562. A pin holder 563 is fixedly engaged with the cap 561. An engaging portion 564 is unitarily formed at the center of the pin holder 563. At the pin holder 563, two pushing pins 565 are fixed around the engaging portion 564. Further, a penetrating hole 566 is formed in the pin holder 563 and the engaging portion 564. A liquid supply path, which is provided in the handle portion 12, extending to the tip of the insert portion 11, is connected with the penetrating hole 566.

Figure 19:
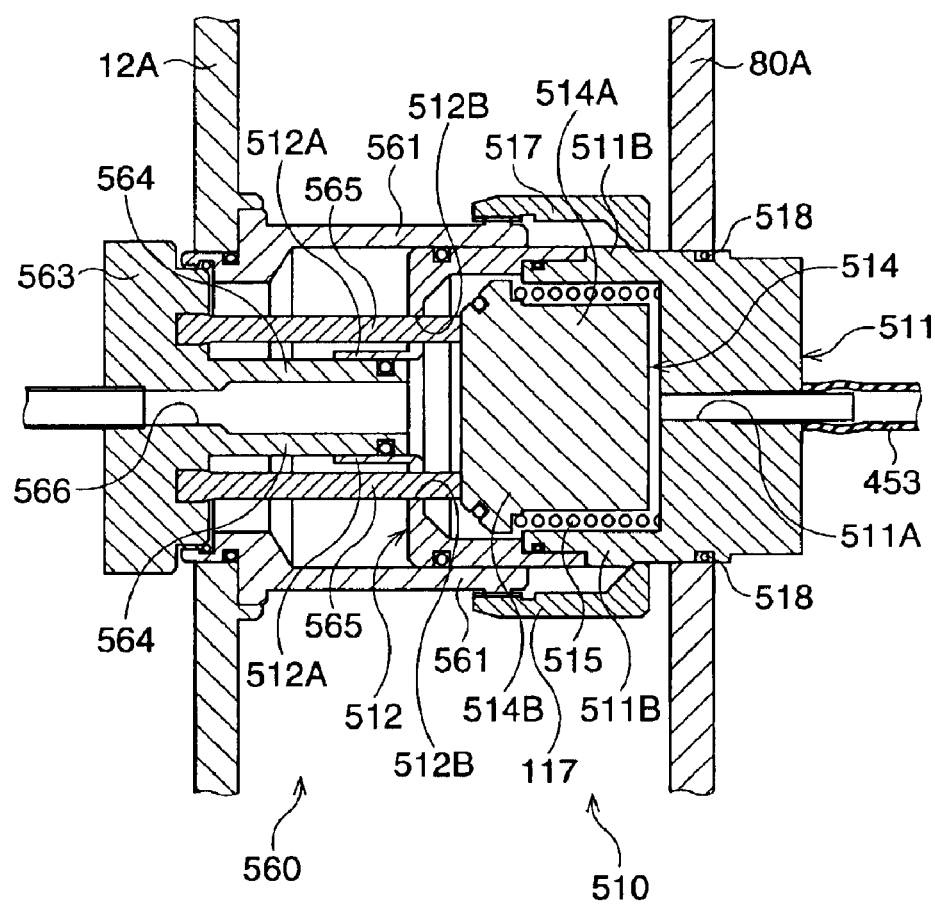
FIG. 19 is a longitudinal sectional view of the liquid supply path connector which is connected with the liquid supply cap portion.

FIG. 19 is a longitudinal sectional view of the liquid supply path connector 510 which is connected with the liquid supply cap portion 560. The cap 561 of the cap portion 560 is inserted into the gap between the covering member 512 and the mounting ring 517 of the connector 510, with the covering member 512 being engaged with the cap 561. Further, the engaged portion 512A of the connector 510 is engaged with the engaging portion 564 of the cap portion 560. Further, the pushing pins 565 respectively pierce through the corresponding holes 512B of the connector 510, pushing the pushed portion 514B of the valve body 514 against the urging force of the coil spring 515. Accordingly, the valve body 514 is moved to the right in FIG. 19, so that a gap is formed between the covering member 512 and the valve body 514.

Namely, when the connector 510 is connected with the cap portion 560, a course in which the liquid can flow is formed between the tube 453 and the penetrating hole 566 which is connected with a liquid supply path of the handle portion 12. The course consists of the gap between the fixing member 511 and the valve body 514, the gap between the covering member 512 and the valve 514, and the opening of the covering member 512.

Note that, as the structures of the air supply path connector 520 and the air supply cap portion 570 are respectively similar to those of the connector 510 and since the cap portion 560, and the connector 520 and the cap portion 570 are connected as shown in FIG. 19, explanations of the connector 510 and the cap portion 570 are omitted.

Figure 20:
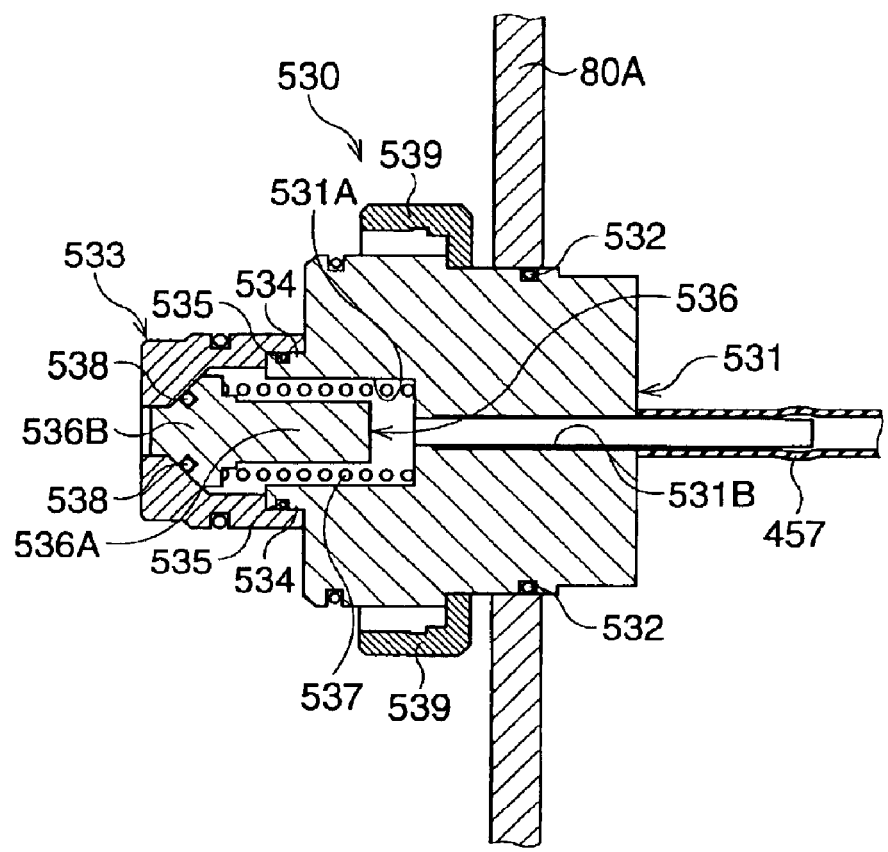
FIG. 20 is a longitudinal sectional view of an inlet connector.

FIG. 20 is a longitudinal sectional view of the inlet connector 530. A cylindrical fixing member 531 is fixedly engaged with an opening which is formed at the side surface 80A of the main body 80. An O-ring 532 is provided between the fixing member 531 and the side surface 80A, so that the engagement of the fixing member 531 is watertight. A recess portion 531A, which has a predetermined depth, is formed at an end of the fixing member 531. A penetrating hole 531B is formed at an axis of the fixing member 531. The inlet tube 451, which supplies air to the pump 82, is connected with the penetrating hole 531B through a connecting member. Further, the penetrating hole 531B is open at the bottom of the recess portion 531A.

A generally cylindrical-shaped covering member 533 is positioned so as to cover the recess portion 531A of the fixing member 531. A mounting portion 534, which is ring-shaped, is formed at the periphery of the opening of the recess portion 531A. The covering member 533 is engaged with the mounting portion 534 through an O-ring 535. An opening is formed at the center of the bottom of the covering member 533.

A generally cylindrical valve body 536 is placed in a space which is formed by a hollow in the covering member 533 and the recess portion 531A. The outer diameter of a base portion 536A of the valve body 536 is slightly smaller than the inner diameter of the recess portion 531A of the fixing member 531 and the inner diameter of the covering member 533, so that a gap exists between the fixing member 531, the covering member 533 and the base portion 536A. The shape of a pushed portion 536B of the valve body 536 and the shape of an inner wall at the bottom of the covering member 533 and its vicinity are complementary to each other.

A coil spring 537 is provided around the outer surface of the base portion 536A of the valve body 536. One end of the coil spring 537 is in contact with the bottom of the recess portion 531A of the fixing member 531, and the other end of the coil spring 537 is in contact with the pushed portion 536B of the valve body 536. The coil spring 537 urges the valve body 536 to the left in FIG. 20. Accordingly, without external force, the opening of the covering member 533 is closed by the valve body 536 at all times.

Further, an O-ring 538 is provided at a portion of the pushed portion 536B which is in contact with the covering member 533 while the valve body 536 is urged by the coil spring 537. Accordingly, the connection between the valve body 536 and the covering member 533 is watertight, when the valve body 536 covers the opening of the covering member 533 because of the urging force of the coil spring 537.

A mounting ring 539 is fixed on the outer surface of the fixing member 531. The mounting ring 539 is arranged such that a predetermined gap exists between the mounting ring 539 and the fixing member 531.

Figure 21:
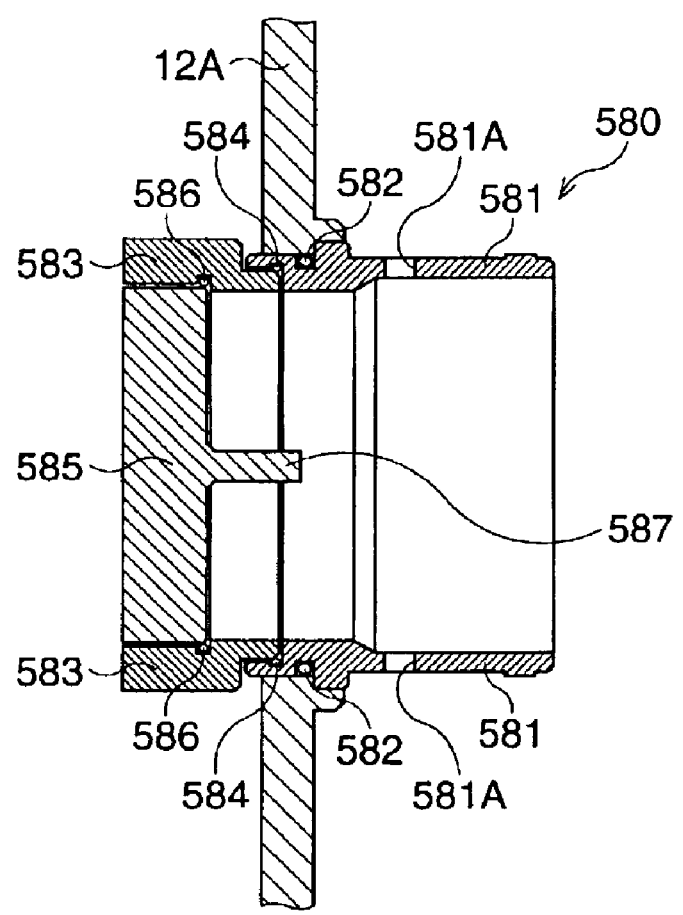
FIG. 21 is a longitudinal sectional view of an inlet cap portion.

FIG. 21 is a longitudinal sectional view of the inlet cap portion 580. A cylindrical cap 581 is provided on the side surface 12A of the handle portion 12. The vicinity of an opening of one end of the cap 581 is fixed to the side surface 12A through an O-ring 582. An inlet 581A for taking in open air is formed at the cap 581. A cylindrical pin holder 583 is fixedly engaged with the cap 581 through an O-ring 584. A generally cylindrical pushing member 585 is fixedly engaged with the pin holder 583 through an O-ring 586. A pushing pin 587 is unitarily formed at the center of the pushing member 585.

Figure 22:
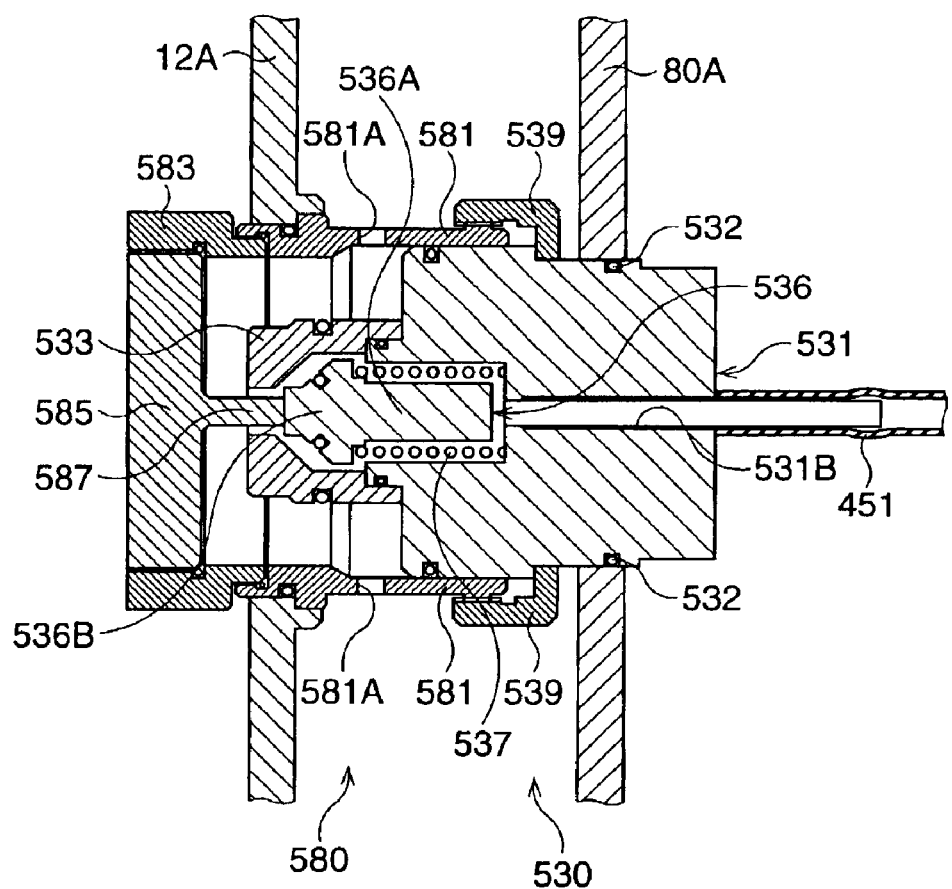
FIG. 22 is a longitudinal sectional view of an inlet connector which is connected with the inlet cap portion.

FIG. 22 is a longitudinal sectional view of the inlet connector 530 which is connected with the inlet cap portion 580. The cap 581 of the cap portion 580 is inserted into the gap between the fixing member 531 and the mounting ring 539 of the connector 530, with the fixing member 531 being engaged with the cap 581. The pushing pin 587 of the cap portion 580 is inserted in the opening of the covering member 533 of the connector 530, and pushes the pushed portion 536B of the valve body 536 against the urging force of the coil spring 537. Accordingly, the valve body 536 is moved to the right in FIG. 22, so that a gap is formed between the covering member 533 and the valve body 536.

Namely, when the connector 530 is connected with the cap portion 580, a course in which the air can flow is formed between the inlet 581A and the tube 451. The course consists of: a space formed by the cap 581 and the covering member 533 and the fixing member 531; the opening of the covering member 533; and the gap between the covering member 533, the fixing member 531, and the valve body 536.

When the fiber scope 450 is used, the pump 82 works at all times. As the course in which the air can flow exists, the open air is taken in at the inlet 581A by the pump 82, and flows to the pump 82 through the tube 451, and is sent into the tank 81 through the tube 452.

The air, which is sent into the tank 81, is sent to the air supply path of the handle portion 12 through the course which is formed between the connector 520 and the cap portion 570. In this state, if the upper hole of the button 71 is covered, the air, which is sent to the air supply path, is sent to the nozzle 51, so that the air is spouted from the nozzle 51.

Further, when the button 71 is pushed, the air, which is sent to the tank 81, can not be discharged. Accordingly, an atmospheric pressure inside the tank 81 rises, so that the liquid stored in the tank 81 is sent out through the tube 453. The liquid, which is sent out through the tube 453, is led to the liquid supply path of the handle portion 12 through the course which is formed between the connector 510 and the cap portion 560, and is sent to the nozzle 52. Consequently, as described above, the liquid is spouted from the liquid supply nozzle 52.

Figure 23:
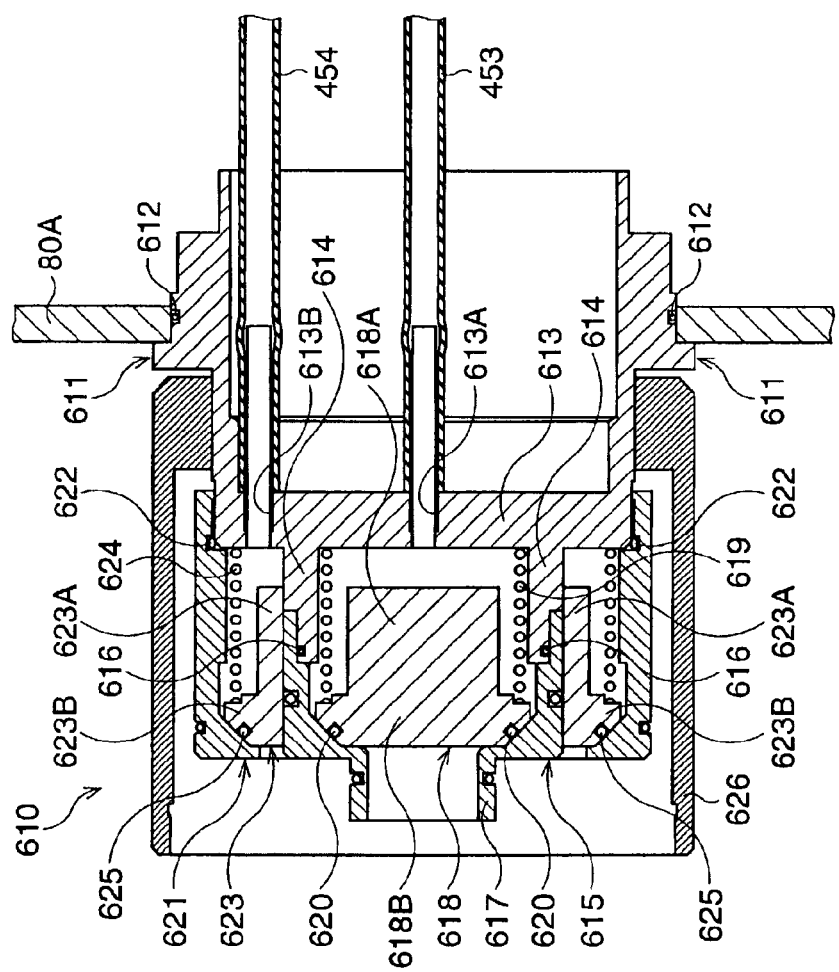
FIG. 23 is a longitudinal sectional view of an air and water sending connector of an endoscope to which a seventh embodiment, according to the present invention, is applied.

FIG. 23 is a longitudinal sectional view of an air and liquid supply connector 610 of an endoscope to which a seventh embodiment, according to the present invention, is applied. Note that, the structures of the endoscope of the seventh embodiment, except for the connector 610 and a cap portion which is connected with the connector 610, are similar to those of the first and the sixth embodiments.

A generally cylindrical fixing member 611 is fixedly engaged with a hole which is formed in the side surface 80A of the main body 80. An O-ring 612 is provided between the fixing member 611 and the main body 80, so that the engagement between the fixing member 611 and the hole of the side surface 80A is water tight. Penetrating holes 613A and 613B are formed at a bottom 613, of the fixing member 611, which is outside the main body 80. The tube 453 is connected with the hole 613A through a connecting cylinder, and the air supply tube 454 is connected with the hole 613B through a connecting cylinder. A wall portion 614, which has a predetermined height, is unitarily formed on the outer surface of the bottom 613. A recess portion is formed by the bottom 613 and the wall portion 614.

A first covering member 615, which is cylindrically shaped, is fixedly engaged with the wall portion 614 through an O-ring 616. The outer diameters of the wall portion 614 and the first covering member 615 are identical, so that the outer surfaces of the wall portion 614 and the covering member 615 do not form a step. An opening is formed at the center of the bottom of the first covering member 615. An engaging portion 617, which is ring-shaped, is formed at the periphery of the opening, projecting toward a side opposite to the fixing member 611.

A valve body 618 is situated in a space which is formed by the above-mentioned recess portion of the fixing member 611 and a hollow of the first covering member 615. The valve body 618 is generally cylindrical. The outer diameter of a base portion 618A of the valve body 618 is slightly smaller than the inner diameters of the wall portion 614 of the fixing member 611 and the first covering member 615, so that a gap exists between the wall portion 614 of the fixing member 611, the first covering member 615, and the base portion 618A. The shape of a pushed portion 618B of the valve body 618 and the shape of an inner wall of the bottom of the first covering member 615 and its vicinity are complementary to each other.

A coil spring 619 is provided around the outer surface of the base portion 618A of the valve body 618. One end of the coil spring 619 is in contact with the bottom 613-of the fixing member 611, and the other end of the coil spring 619 is in contact with the pushed portion 618B of the valve body 618. The coil spring 619 urges the valve body 618 to the left in FIG. 23. Accordingly, without external force, the opening of the first covering member 615 is closed by the valve body 618 at all times.

Further, an O-ring 620 is provided at the pushed portion 618B, so that the connection between the valve body 618 and the first covering member 615 is watertight, when the valve body 618 covers the opening of the first covering member 615 due to the urging force of the coil spring 619 as shown in FIG. 23.

A second covering member 621, which is generally cylindrically shaped, is fixedly engaged with the bottom 613 of the fixing member 611 through an O-ring 622, so as to surround the wall portion 614 of the fixing member 611 and the first covering member 615. An opening is formed at the bottom of the second covering member 621. The bottom of the first covering member 615 is positioned in the opening.

A cylindrical valve body 623 is engaged with a composite wall member consisting of the wall portion 614 and the first covering member 615, in such a manner that the valve body 623 can be slidably moved along its axis. In other words, the engaging object of the wall portion 614 and the first covering member 615, in which the valve body 618 is placed, is provided in the valve body 623, being nested.

The outer diameter of the base portion 623A of the valve body 623 is smaller than the inner diameter of the second covering member 621, so that a gap is formed between the valve body 623 and the second covering member 621. Further, the shape of a pushed portion 623B and the shape of the inner wall of the second covering member 621 are complementary to each other.

A coil spring 624 is provided around the base portion 623A of the valve body 623. One end of the coil spring 624 is in contact with the bottom 613 of the fixing member 611, and the other end of the coil spring 624 is in contact with the pushed portion 623B of the valve body 623. The coil spring 624 urges the valve body 623 to the left in FIG. 23. Accordingly, without external force, the opening of the second covering member 621 is closed by the valve body 623 at all times.

Further, an O-ring 625 is provided at a portion of the pushed portion 623B which is in contact with the second covering member 621 while the valve body 623 is urged by the coil spring 624. Accordingly, the connection between the valve body 623 and the second covering member 621 is watertight, when the valve body 623 covers the opening of the second covering member 621 due to the urging force of the coil spring 624.

A mounting ring 626 is fixed on the outer surface of the fixing member 611. The mounting ring 626 is arranged such that a predetermined gap is formed between the mounting ring 626 and the outer surface of the second covering member 621.

Figure 24:
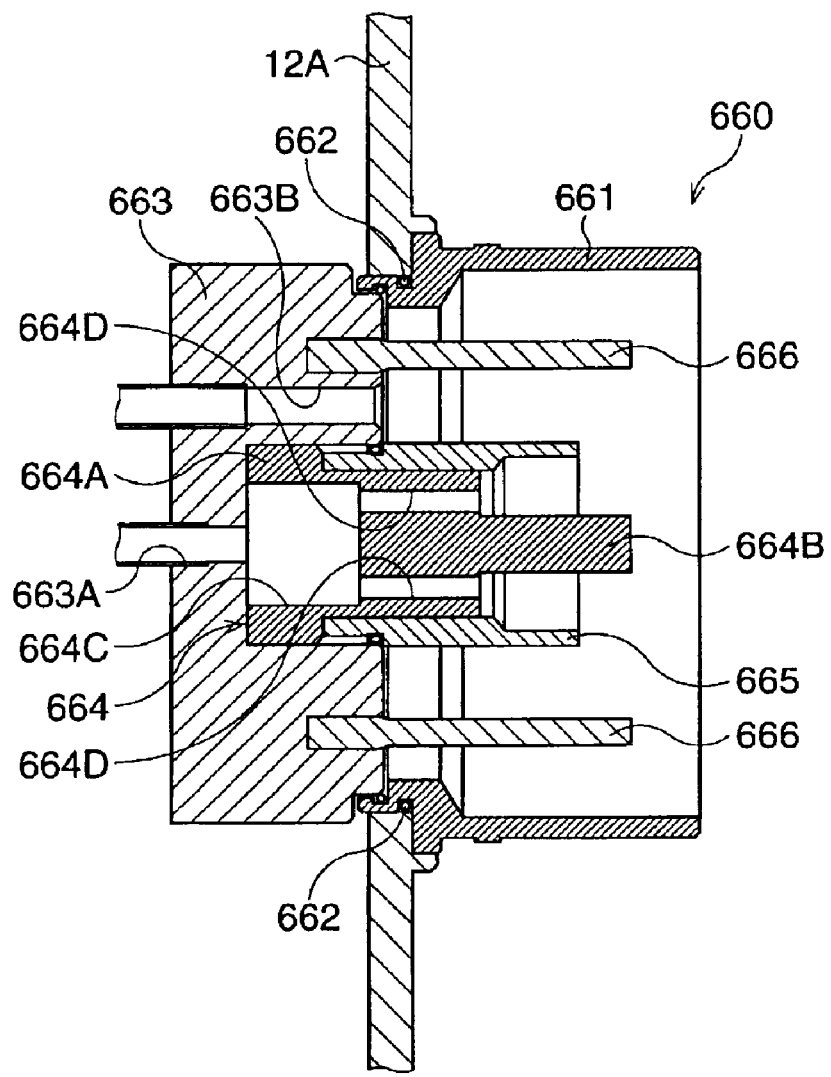
FIG. 24 is a longitudinal sectional view of an air and liquid supply cap portion of the seventh embodiment.

FIG. 24 is a longitudinal sectional view of an air and liquid supply cap portion 660 with which the connector 610 is to be connected. A cylindrical cap 661 is provided at the side surface 12A of the grip portion 14. The vicinity of an opening of one end of the cap 661 is fixed to the side surface 12A through an O-ring 662. A cylindrical pin holder 663 is fixedly engaged with the cap 661. A recess portion, which has a predetermined depth, is formed at the center of the pin holder 663.

A first pushing pin 664 is provided in the recess portion. The first pushing pin 664 includes a cylindrical base body 664A and a cylindrical projecting portion 664B which projects from the base body 664A. The base body 664A includes a large-diameter portion which is fixed to the recess portion of the pin holder 663 and a small-diameter portion, the diameter of which is smaller than that of the large-diameter portion. A gap, which is ring-shaped, is formed between the pin holder 663 and the small-diameter portion.

In the base body 664A, a hole 664C, which has a predetermined depth, is formed at a side opposite to the side on which the projecting portion 664B is formed. Two holes 664D are formed in the small-diameter portion of the base body 664A, so as to pierce through the small-diameter portion, extending along the axis of the small-diameter portion. As shown in FIG. 24, the holes 664D lead to the hole 664C.

An engaged cylinder 665 is fixedly engaged with the small-diameter portion of the base body 664A, at the ring-shaped gap between the pin holder 663 and the small-diameter portion of the base body 664A of the first pushing pin 664.

Two cylindrical pushing pins 666 are fixed at the pin holder 663, being around the engaged cylinder 665. Further, two holes 663A and 663B are formed so as to pierce through the pin holder 663, extending along the axis of the pin holder 663. The hole 663A leads to the above-mentioned recess portion of the pin holder 663, namely, the hole 663A leads to the hole 664C of the first pushing pin 664. The liquid supply path of the handle portion 12 is connected to the hole 663A. The hole 663B leads to the inside of the cap 661 and is connected with the air supply path of the handle portion 12.

Figure 25:
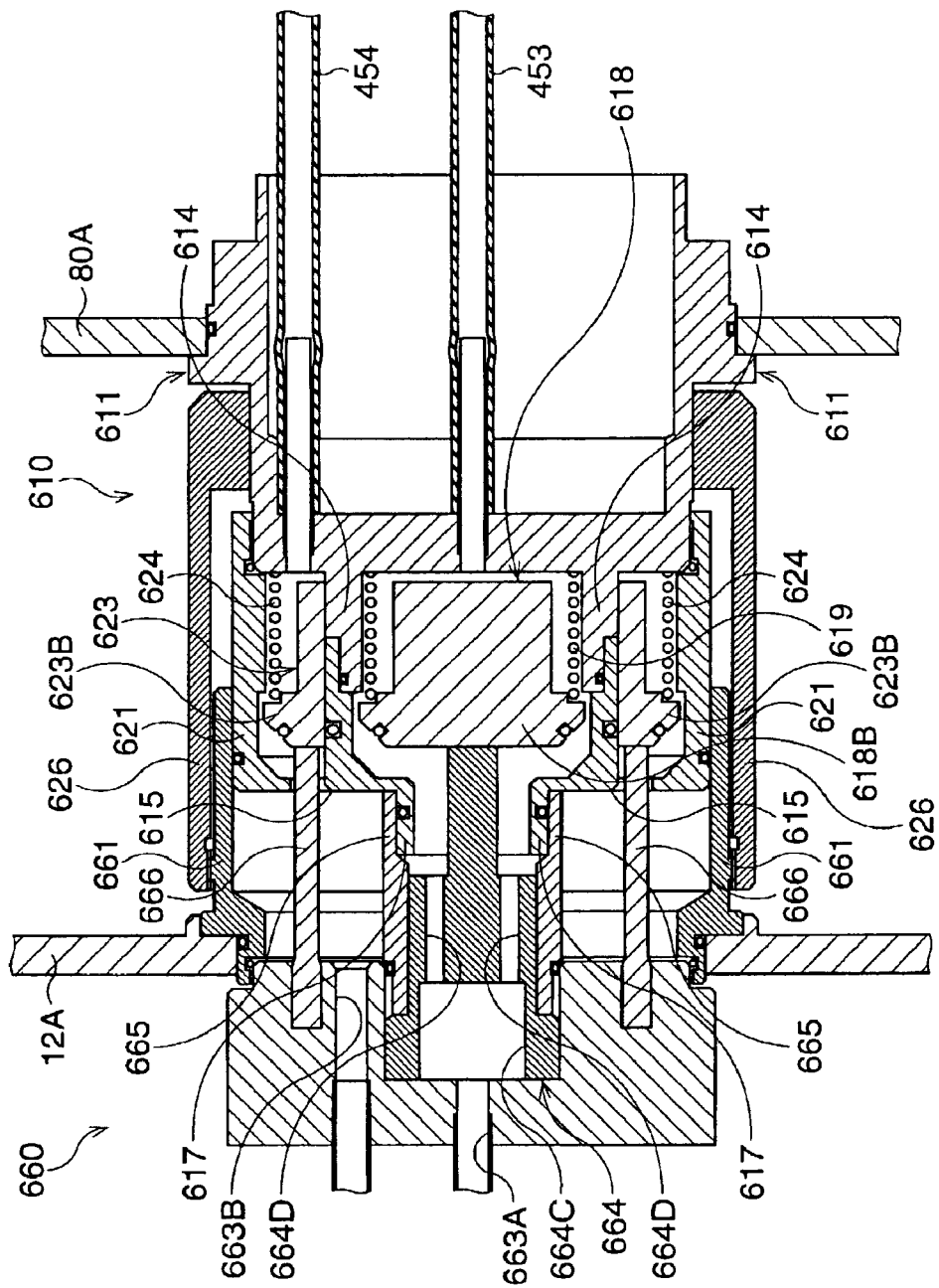
FIG. 25 is a longitudinal sectional view of the connector and the cap portion of the seventh embodiment.

FIG. 25 is a longitudinal sectional view of the connector 610 and the cap portion 660 which are connected. The cap 661 of the cap portion 660 is inserted into the gap between the second covering member 621 and the mounting ring 626 of the connector 610. The cap 661 is engaged with the second covering member 621. Further, the engaged cylinder 665 of the cap portion 660 is engaged with the engaging member 617 of the connector 610.

The first pushing pin 664 of the cap portion 660 pushes the pushed portion 618B of the valve body 618 against the urging force of the coil spring 619, and the valve body 618 is moved to the right in FIG. 25, so that a gap is formed between the first covering member 615 and the valve body 618.

Namely, a course in which the liquid can flow is formed between the tube 453 and the hole 663A. The course consists of the gap between the wall portion 614 of the fixing member 611 and the valve body 618, the gap between the first covering member 615 and the valve body 618, the opening of the first covering member 615, and the holes 664C and 664D in the first pushing pin 664.

Similarly, the second pushing pin 666 of the cap portion 660 pushes the pushed portion 623B of the valve body 623 against the urging force of the coil spring 624, and the valve body 623 is moved to the right in FIG. 25, so that a gap is formed between the second covering member 621 and the valve body 623.

Namely, a course in which air can flow is formed between the tube 454 and the hole 663B with which the air supply path of the handle portion 12 is connected. The course consists of the gap between the second covering member 621 and the valve body 623, the opening of the second covering member 621, the space formed by the cap 661 and the engaged cylinder 665.

Note that, as the structures for supplying the air to the pump 82 in the seventh embodiment are similar to the structures of the inlet connector 530 and the inlet cap portion 580 of the sixth embodiment as shown in FIGS. 20 through 22, the structures for supplying the air to the pump 82 in the seventh embodiment are omitted. Further, the manner in which air is taken in and the liquid and air is supplied to the nozzles 51 and 52, in accordance with the button 71, are similar to the methods used in the sixth embodiment.

Figure 26:
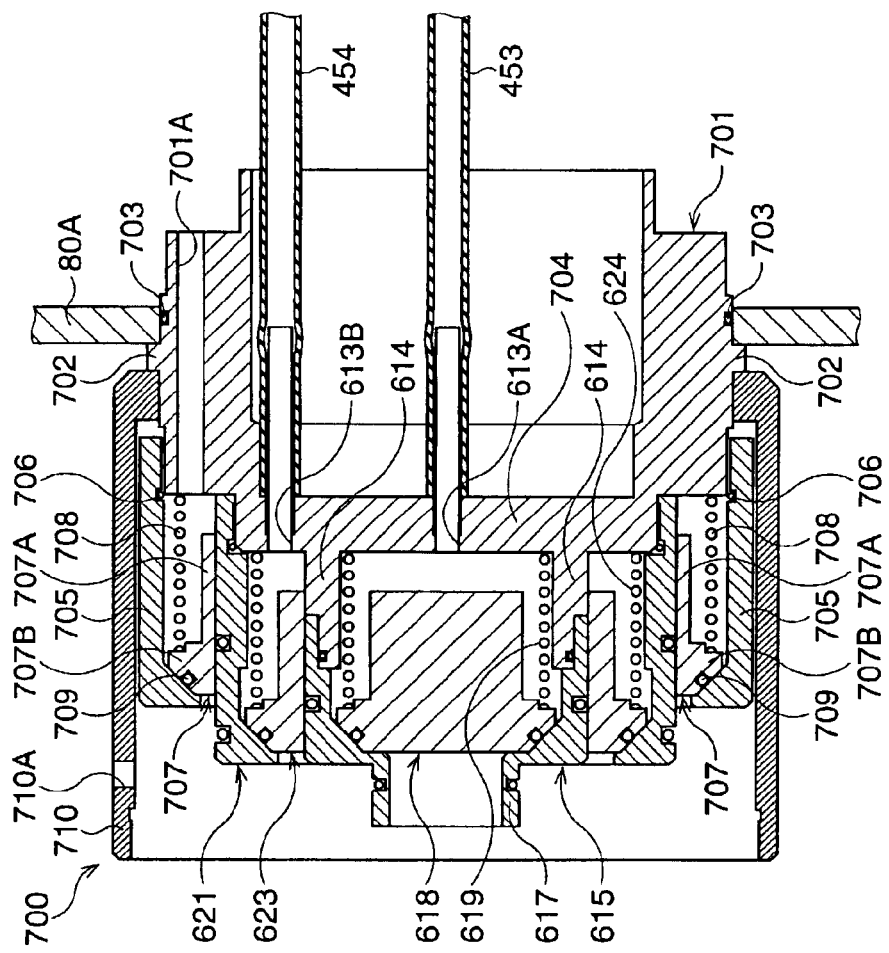
FIG. 26 is a longitudinal sectional view of a connector of a supply unit of a portable endoscope to which an eighth embodiment, according to the present invention, is applied.

FIG. 26 is a longitudinal sectional view of a connector 700 of a supply unit of a portable endoscope to which an eighth embodiment, according to the present invention, is applied. In FIG. 26, with respect to the connector 610, components utilized in the seventh embodiment, which are identical to those in the eighth embodiment, share the same reference numerals.

A fixing member 701 is generally cup-shaped. A cylindrical fixing portion 702 of the fixing member 701 is fixedly engaged with a hole which is formed at the side surface 80A of the main body 80. An O-ring 703 is provided between the fixing portion 702 and the main body 80A, so that the engagement of the fixing portion 702 and the main body 80A is watertight. A bottom 704 of the fixing member 701 is a circular plate which is perpendicular to the axis of the fixing portion 702.

A hole 701A pierces through the fixing portion 702, extending along the axis of the fixing portion 702. One opening of the hole 701A is situated at an end surface of the fixing portion 702 which crosses the outer surface of the bottom 704.

The structure of the wall portion 614 formed on the bottom 704, the first covering member 615, the engaging portion 617, the valve body 618, and the coil spring 619; the structure of the second covering member 621, the valve body 623, and the coil spring 624; and the structure of the holes 613A and 613B formed in the bottom 704; are similar to those of the seventh embodiment.

A third covering member 705, which is generally cylindrically shaped, is fixedly engaged with the outer surface of the fixing portion 702 of the fixing member 701 through an O-ring 706, so as to surround the second covering member 621. An opening is formed at the bottom of the third covering member 705. The second covering member 621 is situated in this opening. A cylindrical valve body 707 is engaged with the second covering member 621 so as to be slidably movable along the axis thereof.

Namely, in the eighth embodiment, the composite wall member consisting of the wall portion 614 and the first covering member 615, in which the valve body 618 is situated, is provided in the valve body 623, being nested, and a composite wall member consisting of the second covering member 621 and the bottom 704, in which the valve body 623 is situated, is provided in the valve body 707, being nested.

The outer diameter of a base portion 707A of the valve body 707 is smaller than the inner diameter of the third covering member 705, so that a gap is formed between the valve body 707 and the third covering member 705. The shape of the pushed portion 707B of the valve body 707 and the shape of the inner wall of the third covering member 705 are complementary to each other.

A coil spring 708 is provided around the base portion 707A of the valve body 707. One end of the coil spring 708 is in contact with the end surface of the fixing portion 702 which crosses the outer surface of the bottom 704. The other end of the coil spring 708 is in contact with the pushed portion 707B of the valve body 707. The coil spring 708 urges the valve body 707 to the left in FIG. 26 at all times. Accordingly, without any external force, the opening of the third covering member 705 is closed by the valve body 707.

Further, an O-ring 709 is provided at a portion of the pushed portion 707B which is in contact with the third covering member 705 while the valve body 707 is urged by the coil spring 708. Accordingly, the connection between the valve body 707 and the third covering member 705 is watertight, when the valve body 707 covers the opening of the third covering member 705 due to the urging force of the coil spring 708.

A mounting ring 710 is fixed on the outer surface of the fixing member 701. The mounting ring 710 is arranged so as to surround the third covering member 705 with a predetermined gap therebetween. An inlet 710A is formed at the mounting ring 710.

Figure 27:
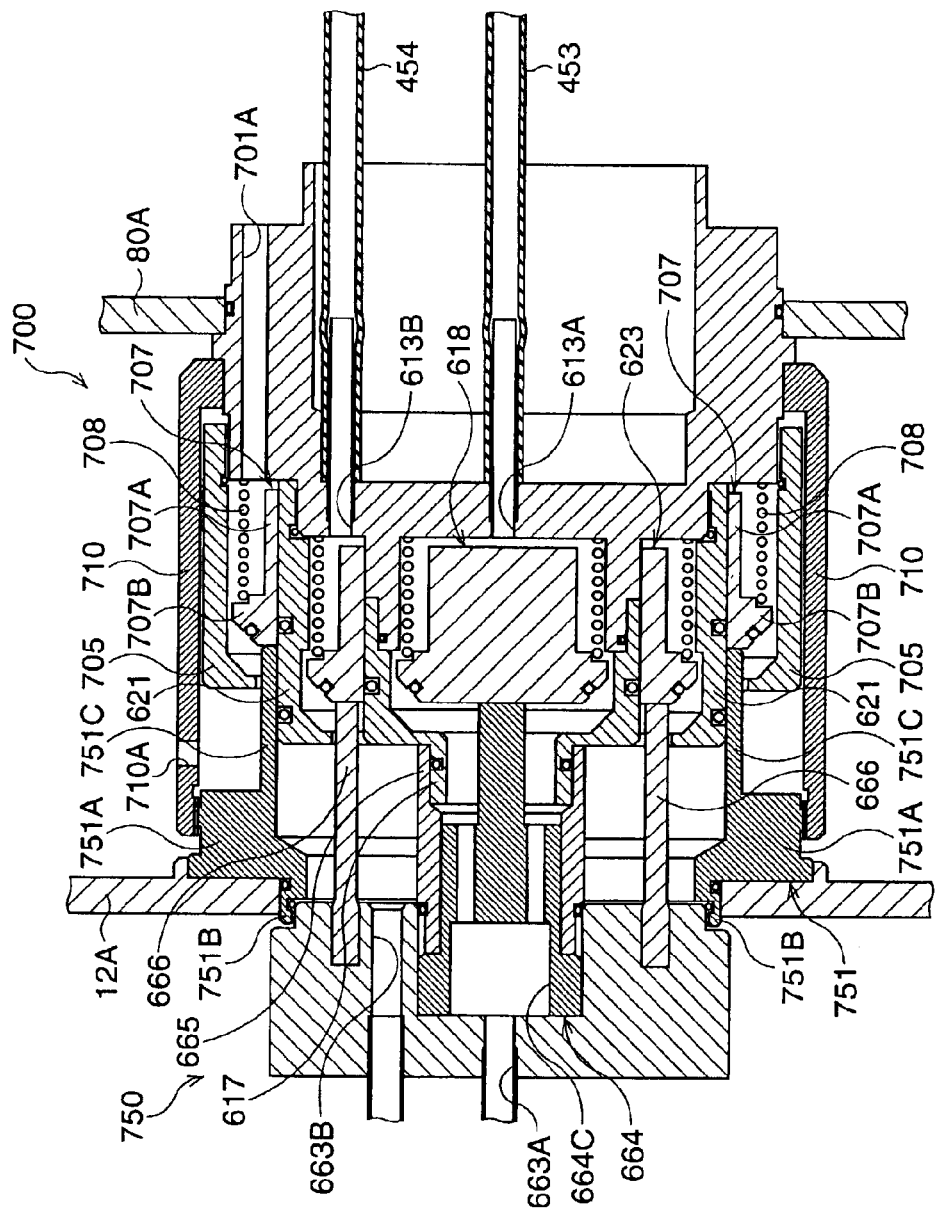
FIG. 27 is a longitudinal sectional view of the connector and a cap portion provided at the handle portion of the eighth embodiment.

FIG. 27 is a longitudinal sectional view of the connector 700 and a cap portion 750 provided at the handle portion 12, which are connected. A generally cylindrical cap 751 includes: a base portion 751A which is situated on the side surface 12A of the handle portion 12; a fixing portion 751B which is engaged with an hole formed at the side surface 12A; and a pushing portion 751C which is formed at the base portion 751A so as to project toward a side opposite to the fixing portion 751B. Note that, the structures of other components of the cap portion 750 except for the cap 751 are similar to those of the cap portion 660 of the seventh embodiment. In FIG. 27, the other components share the same reference numerals as those components of the seventh embodiment.

Similar to the seventh embodiment, the valve bodies 618 and 623 are respectively moved to the right in FIG. 27 by the first pushing pin 664 and the second pushing pins 666, so that the liquid and the air are sent from the tank 81 to the liquid supply path and the air supply path of the handle portion 12.

Further, the pushing portion 751C of the cap 751 is in slidable contact with the outer surface of the second covering member 621 of the connector 700. The end portion of the pushing portion 751C is inserted in the opening of the third covering member 705 being positioned inside. Namely, the pushing portion 751C pushes the pushed portion 707B of the valve body 707 to the right in FIG. 27 against the urging force of the coil spring 708. Accordingly, similar to the valve bodies 618 and 623, the valve body 707 is moved to the right in FIG. 27, so that a gap is formed between the valve body 707 and the third covering member 705.

Namely, a course in which the air can flow is formed between the inlet 710A and the hole 701A with which the inlet tube is connected. The course consists of the space formed by the mounting ring 710 and the cap 751, and the gap between the third covering member 705 and the valve body 707.

While the pump 82 works, the open air is taken in at the inlet 710A through the course formed by the connection between the connector 700 and the cap portion 750, the air is sent to the pump 82, and further is sent from the pump 82 to the tank 81 through the air supply tube 85. Further, the manner in which air is taken in and the liquid and air are supplied to the nozzles 51 and 52, in accordance with the button 71, are similar to the methods of the sixth embodiment.

As described above, according to the sixth through the eighth embodiments, in a state where the supply unit 16 is detached from the handle portion 12, the openings of the above-mentioned covering members of the supply unit 16 are closed by the valve mechanisms which are provided with the valve body and the coil spring. Further, each member is fixed to the side surface 80A of the main body 80 through the O-rings, maintaining watertight connections.

Accordingly, when the supply unit 16 is cleaned after the operation of the scope, it is unnecessary to attach an extra member, for example washing cap, to each covering member, so that steps for cleaning can be omitted. Further, damage to the pump, caused by cleaning without the washing cap, is avoided.

Note that, in the embodiments, two pairs of holes 512B and pushing pins 565, two pairs of holes 664D, and two pairs of second pushing pins 416 are provided. However, more than three pairs of these members can be provided.

Figure 28:
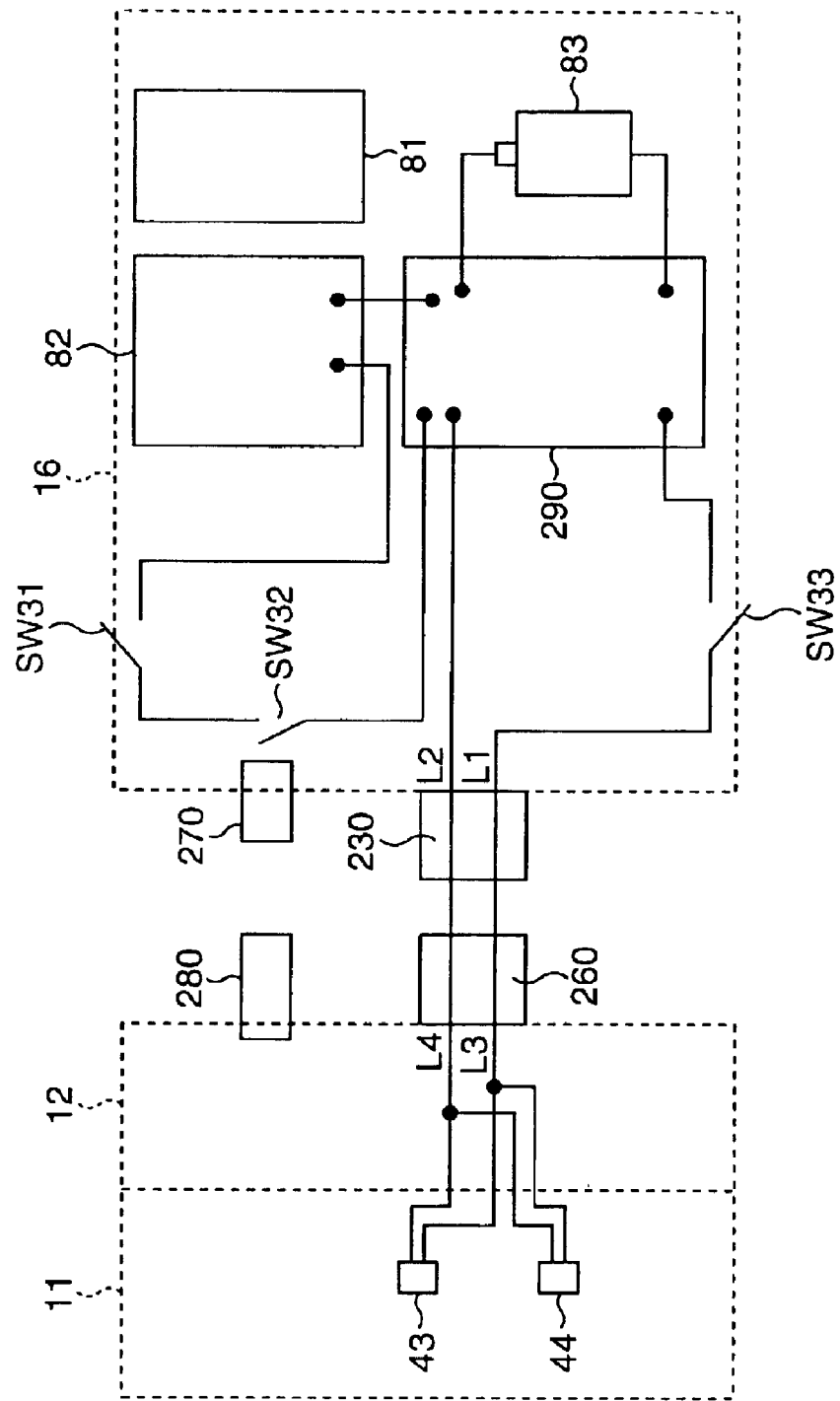
FIG. 28 is a circuit diagram of a fiber scope to which a ninth embodiment, according to the present invention, is applied.

FIG. 28 is a circuit diagram of a fiber scope to which a ninth embodiment, according to the present invention, is applied. Most of components which are included in the fiber scope of the ninth embodiment are similar to those of the first embodiment. Therefore, an explanation of structure of each component is omitted. Further, components utilized in the first embodiment, which are identical to those in the ninth embodiment, share the same reference numerals, in FIG. 28 and the explanation below.

Similar to the first embodiment, the supply unit 16 is provided with the mounting mechanism 210, and the mounting mechanism 210 includes the air and liquid supply cap 220 (omitted in FIG. 28) and the electric connecter cap 230. Also, the grip portion 14 is provided with the mounting mechanism 240, and the mounting mechanism 240 includes the air and liquid supply cap 250 (omitted in FIG. 28) which corresponds to the cap 220 and the electric connecter cap 260 which corresponds to the cap 230. Note that, the structures of the caps 220, 230, 250, and 260 are similar to those of the first embodiment shown in FIG. 6.

Further, in the ninth embodiment, the mounting mechanism 210 includes a pushed button 270, and the mounting mechanism 240 includes a pushing portion 280 which corresponds to the pushed button 270. Further, the supply unit 16 is provided with a pump button and an LED button which are able to be manipulated by the operator.

As shown in FIG. 28, when the supply unit 16 is attached to the handle portion 12, a parallel circuit, in which the pump 82 and the LEDs 43 and 44 are connected with the battery 83, being in parallel, is formed. Driving current of the pump 82 is supplied from the battery 83 to the pump 82 through a voltage regulator 290. Also, driving current for the LEDs 43 and 44 is supplied from the battery 83 to the LEDs 43 and 44 through the voltage regulator 290. The voltage regulator 290 is a circuit for stabilizing the driving currents.

A switch SW31 and a SW32 are provided between the pump 82 and the voltage regulator 290. The state of the switch SW31 is controlled by manipulating the above-mentioned pump button. The switch SW32 is opened, while the supply unit 16 is not attached to the handle portion 12. The switch SW32 is closed, while the supply unit 16 is attached to the handle portion 12 and the pushed button 270 is pushed by the pushing portion 280. When both the switches SW31 and SW32 are closed, the driving current is supplied to the pump 82 from the battery 83. Namely, if the pump button is pushed in a state where the supply unit 16 is attached to the handle portion 12, the driving current is supplied to the pump 82 from the battery 83.

A switch SW33 is provided between the LEDs 43 and 44 and the voltage regulator 290. The state of the switch SW33 is controlled by manipulating the above-mentioned LED button. When the switch SW33 is closed in the state where the supply unit 16 is attached to the grip portion 14, the driving current is supplied to the LEDs 43 and 44 from the battery 83.

Figure 29:
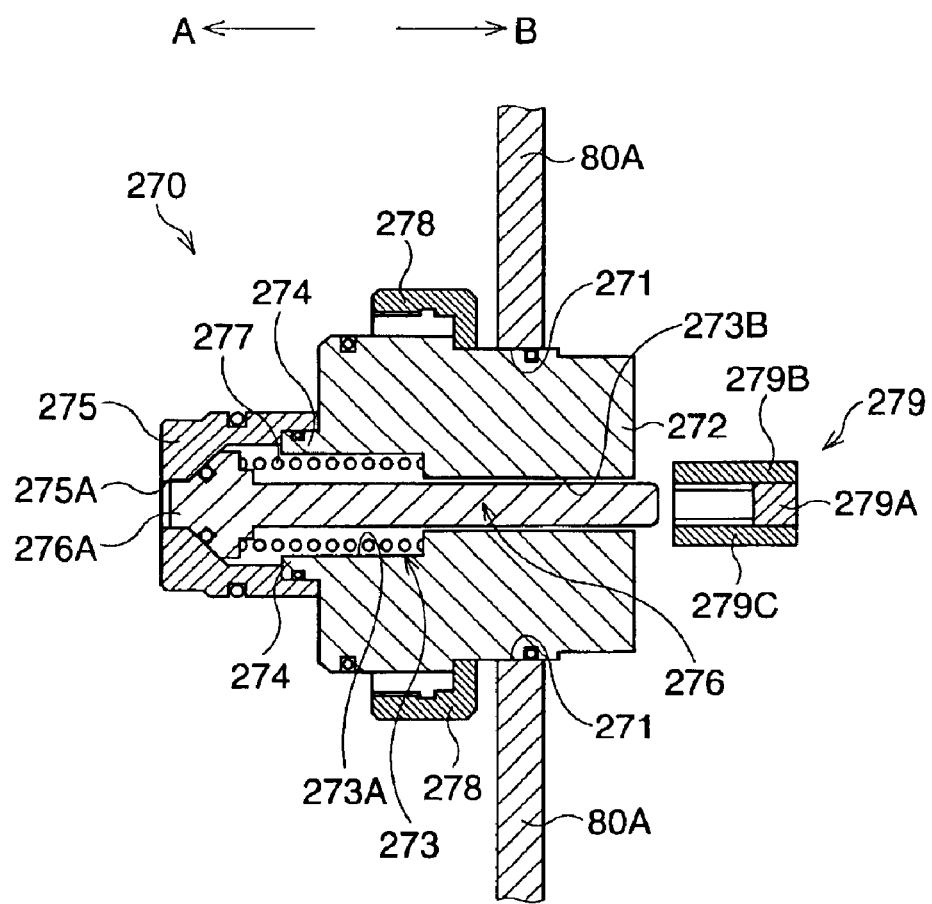
FIG. 29 is an enlarged view of a push button and its vicinity in a state where the supply unit is detached from the handle portion.

FIG. 29 is an enlarged view of the pushed button 270 and its vicinity in a state where the main body 80 is detached from the grip portion 14. An opening 271 is formed at the side surface 80A of the main body 80 of the supply unit 16, similar to the aforementioned openings 221 and 231 of the first embodiment shown in FIG. 6. A fixing member 272, which is generally cylindrically shaped, is engaged with the opening 271 through an O-ring.

A penetrating hole 273 is formed at the axis of the fixing member 272. The penetrating hole 273 includes a large-diameter portion 273A and a small-diameter portion 273B. The large-diameter portion 273A opens outside the main body 80, and the small-diameter portion 273B opens inside the main body 80. In the fixing member 273, a ring-shaped wall portion 274, which has a predetermined height, is unitarily formed at the periphery of the opening of the portion 273A. A cup-shaped covering member 275 is engaged with the wall portion 274 through an O-ring. An opening 275A is formed at the center of the bottom of the covering member 275.

A generally cylindrical pin 276 is provided in the hole 273. The pin 276 is a conductor of electricity. One end of the pin 276 projects outward at the portion 273A. A pushed portion 276A is formed at the tip of the end of the pin 276. The pushed portion 276A and the inner wall of the bottom of the covering member 275 are complementary to each other.

A coil spring 277 is provided around the pin 276 in the portion 273A of the hole 273. One end of the coil spring 277 is in contact with an end surface of a step which is formed by the portions 273A and 273B, and the other end of the coil spring 277 is in contact with the pushed portion 276A of the pin 276, so that the coil spring 277 urges the pin 276 in the direction A in FIG. 29 at all times. Accordingly, as shown in FIG. 29, in the state where the main body 80 is detached from the handle portion 12, the pushed portion 276A of the pin 276 is in contact with the bottom of the covering member 275, and the opening 275A is closed.

A mounting ring 278 is fixed on the outer surface, of the fixing member 272, which is positioned outside the main body 80. A predetermined gap is formed between the mounting ring 278 and the fixing member 272.

Figure 30:
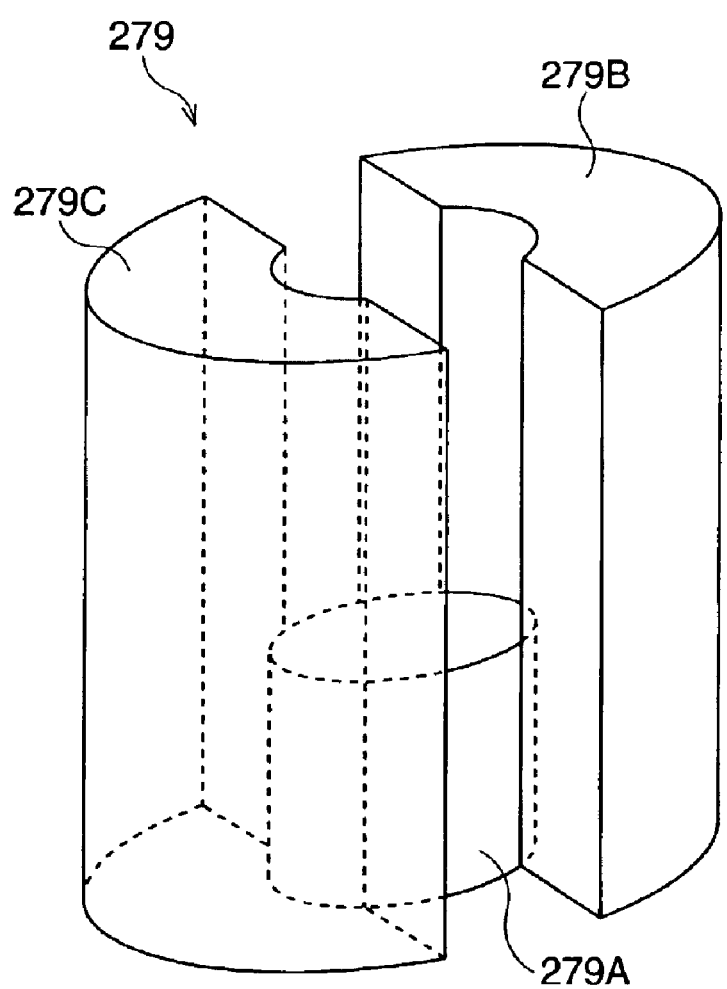
FIG. 30 is a perspective view which shows a pin receiver of the ninth embodiment.

A pin receiver 279 is placed close to the pin 276 which projects outward at the opening of the portion 273B of the hole 273. As shown in FIG. 30, the pin receiver 279 includes a cylindrical-shaped bottom portion 279A, and a pair of contact pieces 279B and 279C. The bottom portion 279A is an insulator, and the contact pieces 279B and 279C are conductors. The contact pieces 279B and 279C are shaped like a half cylinder having a hollow in the middle. The contact pieces 279B and 279C are fixed at the bottom portion 279A in such a manner that the cut end surfaces face each other with a predetermined interval between. The contact piece 279B is connected with the plus terminal of the battery 83 through a lead wire and the voltage regulator 290, and the contact piece 279C is connected with the minus terminal of the battery 83 through a lead wire and the voltage regulator 290.

Figure 31:
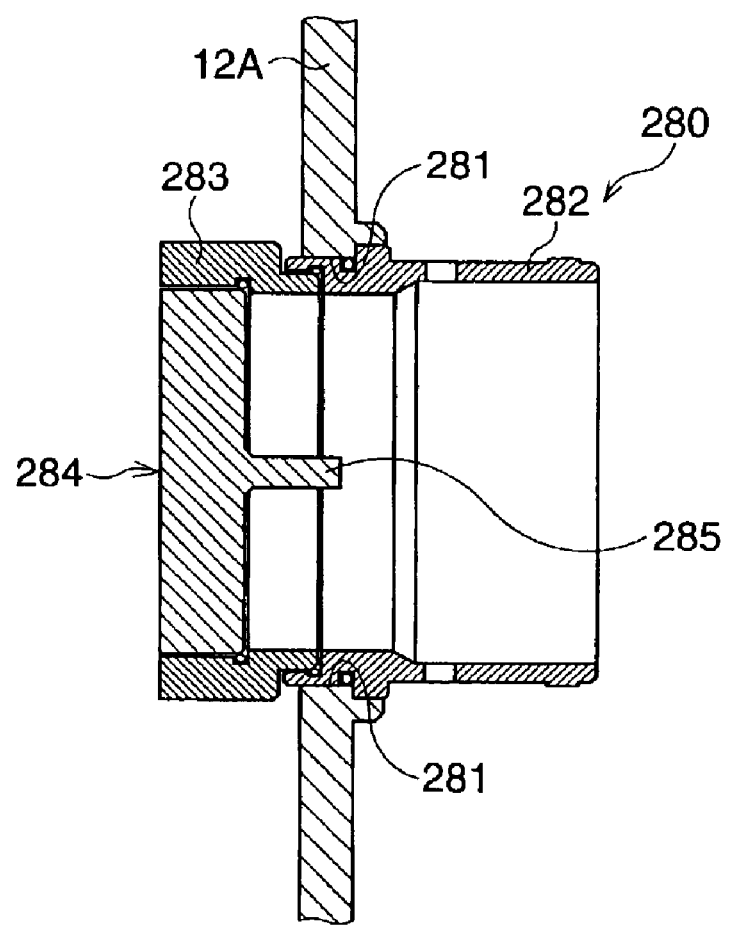
FIG. 31 is an enlarged sectional view of a pushing portion of the ninth embodiment and its vicinity.

FIG. 31 is an enlarged sectional view of the pushing portion 280 of the mounting mechanism 240 and its vicinity. Similar to the openings 251 and 261, an opening 281 is formed in the side surface 12A. A cylindrical cap 282 is fixed at the opening 281 through an O-ring. A cylindrical holding member 283 is fixedly engaged with the opening, of the mounting ring 282, which is close to the opening 281, through an O-ring. A pushing member 284 is fixedly engaged with the holding member 283. At the pushing member 284, a bar-shaped pushing pin 285 is unitarily formed at the center of the end surface close to the mounting ring 282.

Figure 32:
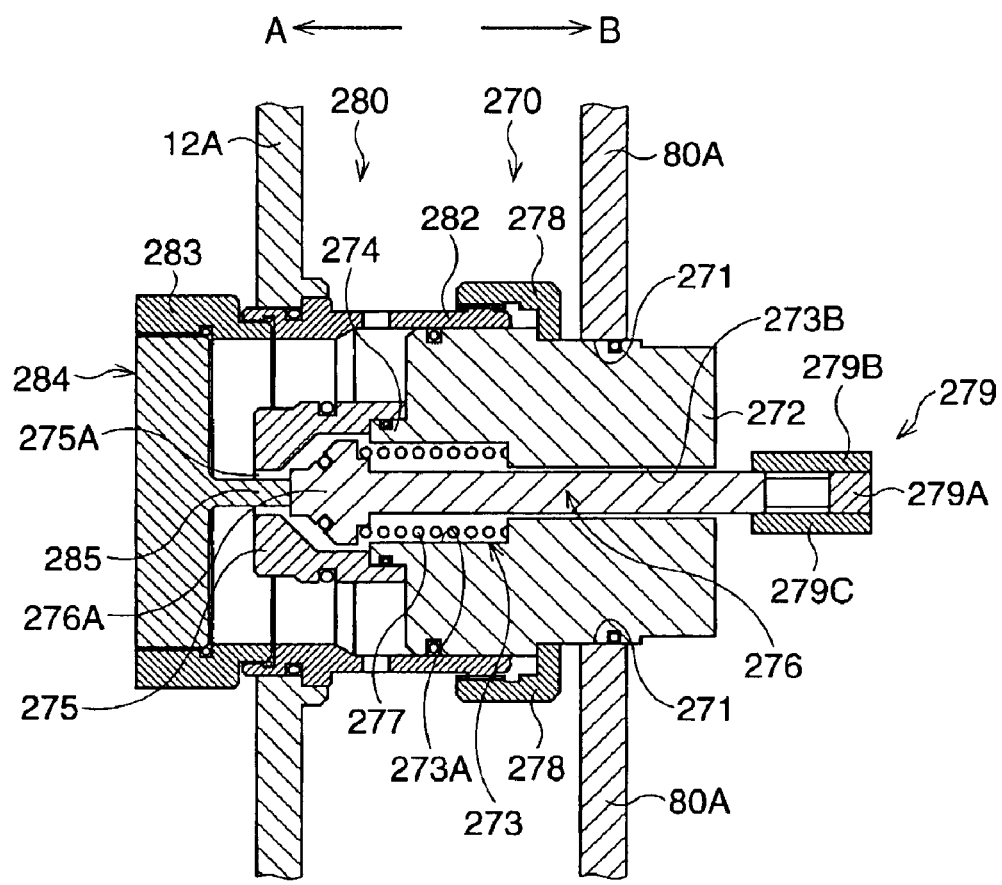
FIG. 32 is an enlarged sectional view of the pushed button and the pushing portion which are connected.

FIG. 32 is an enlarged sectional view of the pushed button 270 and the pushing portion 280 which are connected when the mounting mechanisms 210 and 240 are connected. The mounting ring 282 of the pushing portion 280 is inserted into the gap between the mounting ring 278 and the fixing member 272 of the pushed button 270. The pushing pin 285 of the pushing member 284 is inserted into the covering member 275 through the opening 275A of the covering member 275 of the pushed button 270, pressing the pushed portion 276A of the pin 276 against the urging force of the coil spring 277. Accordingly, the pin 276 is moved in a direction B, and is positioned between the contact pieces 279B and 279C, being in contact with both the contact pieces 279B and 279C.

As described above, the pin 276, and the contact pieces 279B and 279C are conductors. Accordingly, when the end of pin 276 is in contact with the contact pieces 279B and 279C, the lead wires, which are respectively connected with the contact pieces 279B and 279C, are electrically connected. Namely, the switch SW32 is closed.

In a state where the switch SW32 is closed, when the pump button is pushed by the operator and the switch SW31 is closed, the driving current is supplied from the battery 83 to the pump 82. Further, in the state where the caps 230 and 260 are connected, when the LED button is pushed by the operator and the switch SW33 is closed, the driving current is supplied from the battery 83 to the LEDs 43 and 44 which are provided at the tip of the insert portion 11.

To stop the pump 82, the pump button is manipulated to open the switch SW31. Further, when the supply unit 16 is detached from the handle portion 12, the pin 276 is returned to the position shown in FIG. 29. Consequently, the switch SW32 becomes opened, so that the driving current supply from the battery 83 to the pump 82 is stopped and the pump 82 is stopped.

Namely, according to the ninth embodiment, if the operator forgets to manipulate the pump button, and detaches the supply unit 16 in the state where the switch SW32 is open, the pump 82 is automatically stopped. Accordingly, after the supply unit 16 is detached, the pump 82 stops working, and the air is not supplied to the tank 81, so that the liquid does not flow out from the cap 220.

As described above, according to the ninth embodiment, as the supply unit 16 which is provided with the tank 81 is attachably and detachably mounted to the handle portion 12, the portability of the fiber scope is improved, and further, as the pump 82 is automatically stopped after the supply unit 16 is detached, the convenience of handling is improved.

Figure 33:
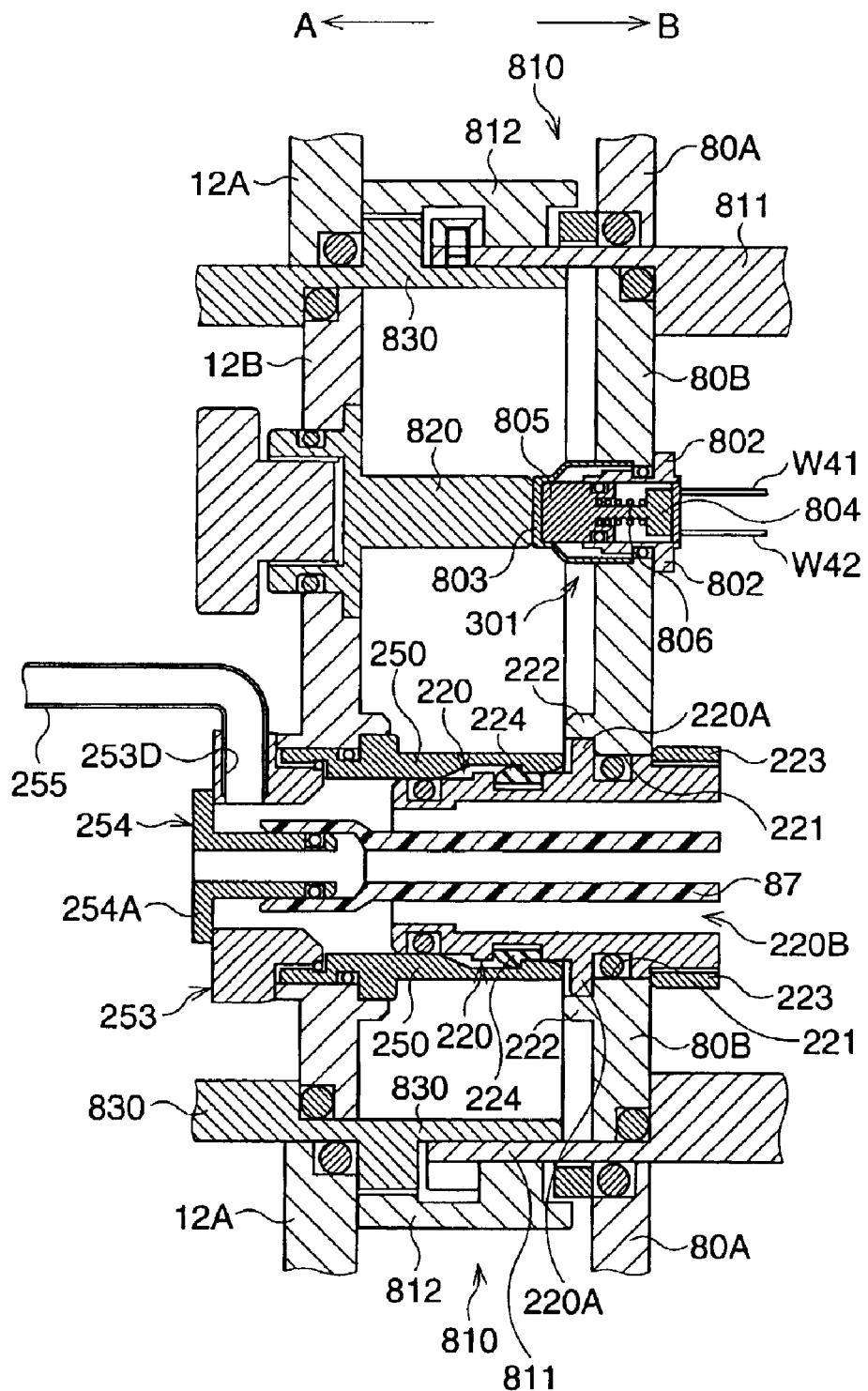
FIG. 33 is a longitudinal sectional view of the connection of the supply unit and the handle portion of a fiber scope to which the tenth embodiment, according to the present invention, is applied.

FIG. 33 is a longitudinal sectional view of the connection of the supply unit and the handle portion of a fiber scope to which the tenth embodiment, according to the present invention, is applied. FIG. 33 mainly shows connecting mechanisms of the grip portion 14 and the supply unit 16. Most of components which are included in the fiber scope of the tenth embodiment are similar to those of the first and ninth embodiments. Also, the electrical circuit of the fiber scope of the tenth embodiment is similar to that of the ninth embodiment. Therefore, explanations of the structure of each component and the electrical circuit are omitted. Further, components utilized in the first and ninth embodiments, which are identical in the tenth embodiment, share the same reference numerals, in FIG. 33 and the explanation below.

A mount supporting cap 810 is provided at the supply unit 16 so as to surround the air and liquid supply cap 220, the electric connecter cap 230, and a pushed button 801. Also, a mount supporting cap 830 is provided at the grip portion 14 of the handle portion 12 so as to surround the air and liquid supply cap 250, the electric connecter cap 260, and a pushing pin 820. Note that, the caps 230 and 260 are omitted in FIG. 33 for clarity.

When the mount supporting caps 810 and 830 are engaged, the caps 220 and 250 are connected, the caps 230 and 260 are connected, and the pushed button 801 is pushed by the pushing pin 820.

Note that, the structures of the mount supporting caps 810 and 830 are similar those of the mount supporting caps 311 and 331 of the third embodiment depicted in FIG. 8. Therefore, explanations of the caps 810 and 830 are omitted. Further, holding plates 80B and 12B are respectively similar to the holding plates 313 and 333 of the third embodiment depicted in FIG. 8.

The pushed button 801 is provided at an opening which is formed close to the cap 220 at the holding plate 80B. A generally cylindrically shaped frame member 802 of the pushed button 801 is mounted in the above-mentioned opening. A cup-shaped protecting member 803, which is made of rubber, is fixed to the frame member 802 by screws. In an inner space of the frame member 802 and the protecting member 803, a switching member 804 and a pushed member 805 which is made of resin, are provided.

The switching member 804 is generally cylindrical, having a large-diameter portion and a small-diameter portion. Also, the pushed member 805 is generally cylindrical, having a large-diameter portion and a small-diameter portion. The small-diameter portions of the switching member 804 and the pushed member 805 face each other, and are coaxial with each other. A coil spring 806 is provided around these small-diameter portions. One end of the coil spring 806 is in contact with a surface of a step formed by the large-diameter portion and the small-diameter portion of the switching member 804. The other end of the coil spring 806 is in contact with a surface of a step formed by the large-diameter portion and the small-diameter portion of the pushed member 805. The coil spring 806 urges the pushed member 805 in the direction A, namely, outside the main body 80.

Further, a lead wire W41 and a lead wire W42 are connected with the switching member 804 by soldering. The lead wire W41 is connected with the plus terminal of the battery 83 through the pump 82 and the switch SW31. The lead wire W42 is connected with the minus terminal of the battery 83 through the voltage regulator 290. The pushed button 801 is constructed such that, when the end surface of the small-diameter portion of the switch 304 and the end surface of the small-diameter portion come in contact, the lead wires 41 and 42 are electrically connected.

At the holding plate 12B of the grip portion 14, a bar-shaped pushing pin 820 is fixed in an opening which is formed close to the cap 250 through an O-ring.

As shown in FIG. 33, in a state where the cap 811 and the cap 830 are engaged with each other, the pushing pin 820 pushes the pushed member 805 of the pushed button 801 in the direction B through the protecting member 803 against the urging force of the coil spring 806. Consequently, the end surface of the small-diameter portion of the pushed member 805 and the end surface of the small-diameter portion of the switching member 804 come in contact, and the lead wires 41 and 42 are electrically connected. Namely, the switch SW32 (see FIG. 28) becomes closed. In the state where the switch SW32 is closed, if the operator pushes the pump button and the switch SW31 becomes closed, the driving current supply from the battery 83 to the pump 82 is started.

If the supply unit 16 is detached from the handle portion 12, the pushed member 805 is moved in the direction A because of the urging force of the coil spring 806. Consequently, the end surface of the small-diameter portion of the pushed member 805 and the end surface of the small-diameter portion of the switching member 804 are separated, the electrical continuity between the lead wires 41 and 42 is canceled, and the switch SW32 is opened. Accordingly, the driving current supply from the battery 83 to the pump 82 is automatically stopped. Namely, according to the tenth embodiment, the effect similar to that of the ninth embodiment can be obtained.

Figure 34:
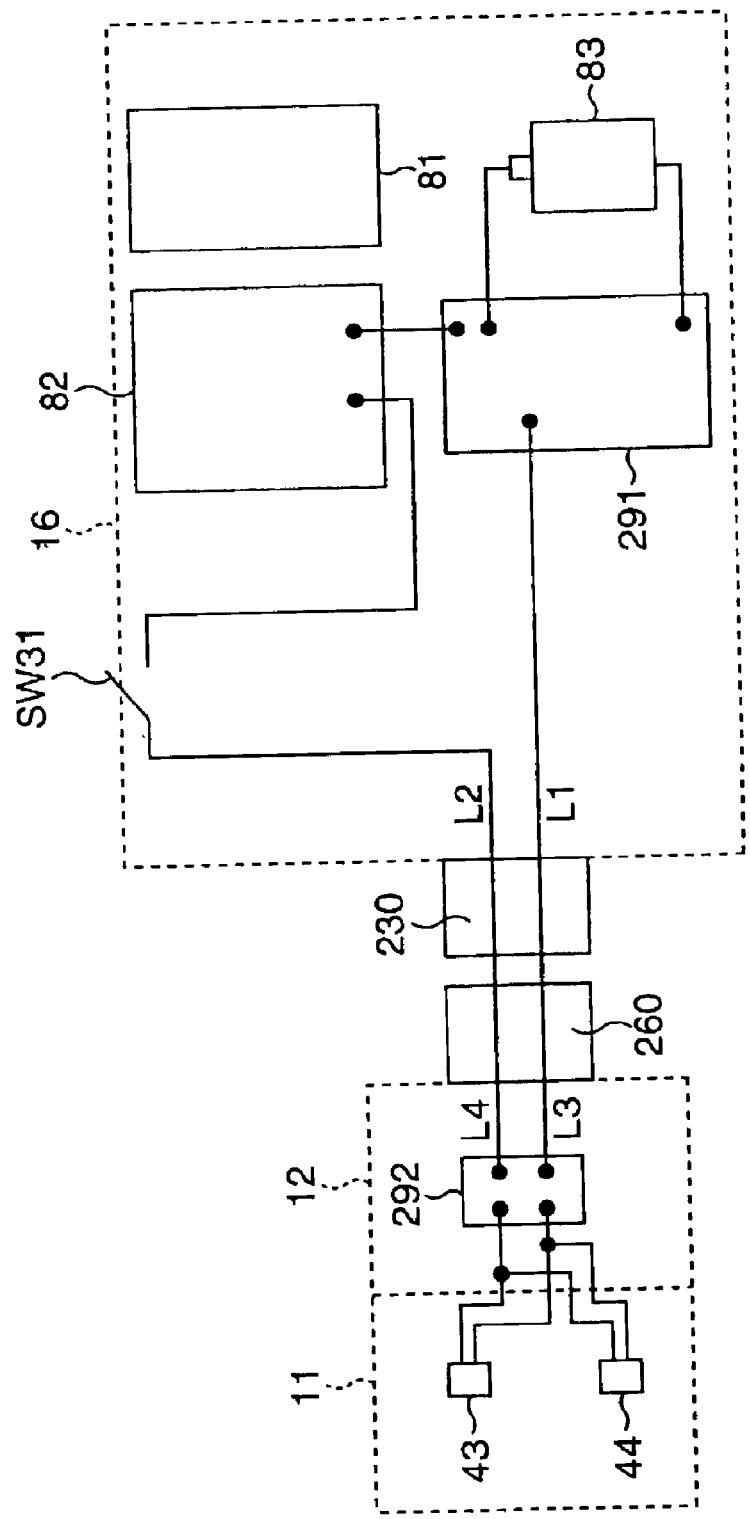
FIG. 34 is a circuit diagram of a fiber scope to which an eleventh embodiment, according to the present invention, is applied.

FIG. 34 is a circuit diagram of a fiber scope to which an eleventh embodiment, according to the present invention, is applied. Note that, the mechanical structures of the fiber scope of the eleventh embodiment are similar to those of the fiber scope 200 of the second embodiment depicted in FIG. 5, except for the button 85. Therefore, an explanation of structure of each component is omitted. Further, components utilized in the second and ninth embodiments, which are identical to those in the eleventh embodiment, share the same reference numerals, in FIG. 34 and the explanation below.

In the eleventh embodiment, the state of the switch SW31 is controlled in accordance with the manipulation of the pump button 86.

In the supply unit 16, the lead wire L2 is connected with the plus terminal of the battery 83 through the switch SW31, the pump 82 and a voltage regulator 291, and the lead wire L1 is connected with the minus terminal of the battery 83 through the voltage regulator 291. The voltage regulator 291 is a circuit for stabilizing the driving current of the pump 82.

In the fiber scope, the lead wire L3 is connected with the LEDs 43 and 44 through a voltage regulator 292, and the lead wire L4 is also connected with the LEDs 43 and 44 through the voltage regulator 292. The voltage regulator 292 is a circuit for stabilizing the driving current of the LEDs 43 and 44.

When the supply unit 16 is attached to the handle portion 12, and the caps 230 and 260 are connected, the lead wires L1 and L3 are electrically continued, and the lead wires L2 and L4 are electrically continued. Namely, a circuit, in which the battery 83, the pump 82, the switch SW31, the LEDs 43 and 44, and the voltage regulators 290 and 291 are connected in series, is formed. Accordingly, in this state, if the pump button 85 is pushed and the switch SW31 becomes closed, the driving current is supplied from the battery 83 to the pump 82 and the LEDs 43 and 44.

When the supply unit 16 is detached from the handle portion 12, and the caps 230 and 260 are disconnected, the connection between the contact pins 266 and 238 are canceled, and the contact between the contact pins 267 and 239 is canceled. Namely, the electrical continuity between the lead wires L1 and L3, and the electrical continuity between the lead wires L2 and L4, are canceled, so that the above-mentioned series circuit is disconnected. Consequently, the driving current supply from the battery 83 to the pump 82 and the LEDs 43 and 44 is automatically stopped. Accordingly, if the supply unit 16 is detached from the handle portion 12 in the state where the switch SW31 is closed, the liquid does not flow out from the tank 81 because the pump 82 has ceased to work.

According to the ninth through eleventh embodiments, the supply unit 16 can be attachably and detachably mounted to the handle portion 12, and further, when the supply unit 16 is detached from the handle portion 12, the pump 82 is automatically stopped. Accordingly, the portability of the fiber scope is improved, and further the convenience of handling is improved, because the pump 82 is automatically stopped when the supply unit 16 is detached and the flow of the liquid out of the tank 81 is prevented.

As described above, according to the present invention, the portability of the endoscope and the convenience of handling the endoscope are improved.

The present disclosure relates to subject matters contained in Japanese Patent Applications Nos. P2001-218109 (filed on Jul. 18, 2001), P2001-218043 (filed on Jul. 18, 2001) P2001-293478 (filed on Sep. 26, 2001), and P2001-333796 (filed on Oct. 31, 2001) which are expressly incorporated herein, by references, in their entirety.

What is claimed is:

1. A portable endoscope comprising:
   a semiconductor light-emitting element that is provided at a tip of an insert portion of a scope in order to illuminate the area to be observed; and
   a supply unit that includes: a pump which supplies gas and liquid to said tip; a power supplying apparatus which supplies power to said semiconductor light-emitting element and said pump; and a tank in which said liquid is stored;
   wherein said supply unit is provided on a handle portion of said scope.

2. A portable endoscope according to claim 1, wherein said supply unit is fixed to said handle portion.

3. A portable endoscope according to claim 1, wherein said supply unit is attachably and detachably mounted on said handle portion.

4. A portable endoscope according to claim 1, wherein said supply unit is placed so as to extend in a direction which is perpendicular to the longitudinal direction of said handle portion.

5. A portable endoscope according to claim 3, wherein said supply unit includes a first mounting mechanism that is provided with a first connecting portion and a second connecting portion,
   and said handle portion includes a second mounting mechanism that is provided with a third connecting portion which is connectable with said first connecting portion and a fourth connecting portion which is connectable with said second connecting portion,
   wherein when said first and third connecting portions are connected, a gas supply path of said insert portion, which sends said gas to said tip, is connected with said pump, and a liquid supply path of said insert portion, which sends said liquid to said tip, is connected with said tank; and
   when said second and fourth connecting portions are connected, a driving electric current is supplied from said power supplying apparatus to said semiconductor light-emitting element.

6. A portable endoscope according to claim 5, wherein:
   said first connecting portion is a first cylindrical member that is provided on a side surface of said supply unit, and
   said first cylindrical member comprises an opening of a gas supply path, of said supply unit, which is connected with said pump, and an opening of a liquid supply path, of said supply unit, which is connected with said tank;
   said second connecting portion is a second cylindrical member that is provided on said side surface, being close to said first cylindrical member, and a first pair of contact pins, which are electrically connected with said power supplying apparatus, being bear on an end surface of said second cylindrical member;
   said third connecting portion is a first receptive member, being shaped like a round bar, with which said first cylindrical member can be engaged,
   one end of said gas supply path of said insert portion and one end of said liquid supply path of said insert portion are provided in said first receptive member; and
   said fourth connecting portion is a second receptive member, being shaped like a round bar, with which said second cylindrical member can be engaged, and
   a second pair of contact pins, which are connected with said semiconductor light-emitting element through lead wires, being provided in said second receptive member,
   wherein when said first cylindrical member is engaged with said first receptive member, said gas supply path of said supply unit and said gas supply path of said insert portion are connected, and said liquid supply path of said supply unit and said liquid supply path of said insert portion are connected,
   when said second cylindrical member is engaged with said second receptive member, said first pair of contact pins and said second pair of contact pins are in contact.

7. A portable endoscope according to claim 5, wherein said first mounting mechanism includes a first mount-supporting member, being generally ring-shaped, which is provided on said side surface of said supply unit so as to surround said first and second connecting portions,
   said second mounting mechanism includes a second mount-supporting member, being generally ring-shaped, which is formed so as to surround said third and fourth connecting portions, and
   said first and second mount-supporting members are arranged such that said first and third connecting portions are connected and said second and fourth connecting portions are connected, when said first and second mount-supporting members are engaged with each other.

8. A portable endoscope according to claim 1, wherein said power supplying apparatus is attachably and detachably mounted on a handle portion of said scope, and
   said tank and said pump are symmetrically arranged along a longitudinal axis of said handle portion.

9. A portable endoscope according to claim 8, wherein said handle portion includes a grip portion that is gripped by an operator and a linking portion that links said grip portion and said insert portion,
   wherein said tank and said pump are fixed in said linking portion, and said power supplying apparatus is mounted in said grip portion so as to extend in a direction perpendicular to said longitudinal axis of said handle portion.

10. A portable endoscope according to claim 3, wherein said supply unit includes a supply unit connector that has enclosed type valve mechanisms, and said handle portion includes a handle portion connector that has valve opening mechanisms.

11. A portable endoscope according to claim 10, wherein each of said enclosed type valve mechanisms include:
    a valve body;
    a holding member which holds said valve body, said holding member having an opening; and
    an urging member which is provided in said holding member and urges said valve body such that said opening is closed.

12. A portable endoscope according to claim 11, wherein each of said valve opening mechanisms includes a projecting member which presses said valve body in a direction opposite to a direction of the urging force of said urging member, when said supply unit is attached to said handle portion.

13. A portable endoscope according to claim 12, wherein said scope includes a gas supply path for sending gas to said tip and a liquid supply path for sending liquid to said tip, and
when said supply unit is attached to said handle portion:
a fifth connecting portion, of said supply unit connector, which is linked to said pump, and a sixth connecting portion, of said handle portion connector, which is linked to said gas supply path are connected, so that said gas supply path is connected with said pump; and
a seventh connecting portion, of said supply unit connector, which is linked to said tank, and an eighth connecting portion, of said handle portion connector, which is linked to said liquid supply path are connected, so that said liquid supply path is connected with said tank,
said fifth and seventh connecting portions having said enclosed type valve mechanism,
said sixth and eighth connecting portions having said valve opening mechanism.

14. A portable endoscope according to claim 13, wherein said fifth and seventh connecting portions are nested.

15. A portable endoscope according to claim 14, wherein said valve body of said seventh connecting portion has cylindrical shape, and said fifth connecting portion is provided in said valve body of said seventh connecting portion.

16. A portable endoscope according to claim 13, wherein said supply unit connector includes a ninth connecting portion, of said enclosed type valve mechanism, which is linked to said pump, and said handle portion connector includes a tenth connecting portion, of said valve opening mechanism, which is linked to an inlet of said pump, and
when said supply unit is attached to said handle portion, said ninth and tenth connecting portions are connected, so that said pump is linked with said inlet.

17. A portable endoscope according to claim 16, wherein said fifth, seventh, and ninth connecting portions are nested.

18. A portable endoscope according to claim 17, wherein said valve body of said seventh connecting portion and said valve of said ninth connecting portion have a cylindrical shape, and said fifth connecting portion is provided in said valve body of said seventh connecting portion, and said seventh connecting portion is provided in said valve body of said ninth connecting portion.

19. A portable endoscope according to claim 3, wherein when said supply unit is detached from said handle portion, driving current supplied from said power supplying apparatus to said pump is stopped.

20. A portable endoscope according to claim 19, wherein when said supply unit is attached to said handle portion, a parallel circuit, in which said pump and said semiconductor light-emitting element are connected with said power supplying apparatus, is formed.

21. A portable endoscope according to claim 20, wherein said supply unit includes a first switch element which is closed when said supply unit is attached to said handle portion and is opened when said supply unit is detached from said handle portion, wherein
when said first switch element is closed, supplying driving current from said power supplying apparatus to said pump becomes possible, and
when said first switch element is opened, supplying driving current from said power supplying apparatus to said pump is stopped.

22. A portable endoscope according to claim 21, wherein said supply unit includes a second switch element which can be controlled by an operator, and supply of driving current from said power source supplying apparatus to said pump is controlled in accordance with the state of said second switch, and
when both said first and second switch elements are closed, supplying driving current from said power supplying apparatus to said pump is carried out.

23. A portable endoscope according to claim 21, wherein said supply unit includes a push button, and said handle portion includes a pushing member for pushing said push button,
wherein when said supply unit is attached to said handle portion, said push button is pushed by said pushing member, so that said first switch element is closed.

24. A portable endoscope according to claim 20, wherein said supply unit includes a third switch element which exists between said power supplying apparatus and said semiconductor light-emitting element in said parallel circuit.

25. A portable endoscope according to claim 19, wherein when said supply unit is attached to said handle portion, a series circuit, in which said power supplying apparatus, said pump, and said semiconductor light-emitting element are connected in series, is formed.

26. A portable endoscope according to claim 25, wherein said supply unit includes a third switch element which can be controlled by an operator, said third switch element existing in said series circuit, wherein
turning on/off of said semiconductor light-emitting element, and supplying driving current from said power supplying apparatus to said pump are controlled in accordance with the state of said third switch element.

27. A portable endoscope comprises:
means for illuminating the area in front of a tip of an insert portion of a scope, said illuminating means being provided at said tip; and
a supply unit that includes: means for supplying gas and liquid to said tip; means for supplying power to said illuminating means and said gas and liquid supplying means; and means for storing said liquid;
wherein said supply unit is provided on a handle portion of said scope.

* * * * *